United States Patent [19]
Malabarba et al.

[11] Patent Number: 5,648,456
[45] Date of Patent: Jul. 15, 1997

[54] PENTAPEPTIDE ANTIBIOTICS

[75] Inventors: Adriano Malabarba, Binasco; Romeo Ciabatti, Novate Milanese; Jürgen Kurt Kettenring, Varese, all of Italy

[73] Assignee: Gruppo Lepetit S.p.A., Milano, Italy

[21] Appl. No.: 454,807

[22] Filed: May 31, 1995

Related U.S. Application Data

[62] Division of Ser. No. 440,868, May 15, 1995, which is a continuation of Ser. No. 298,237, Aug. 30, 1994, abandoned, which is a continuation of Ser. No. 122,820, Sep. 17, 1993, abandoned, which is a continuation of Ser. No. 961,213, Oct. 15, 1992, abandoned, which is a continuation of Ser. No. 842,799, Feb. 27, 1992, abandoned, which is a continuation of Ser. No. 552,275, Jul. 12, 1990, abandoned.

[30] Foreign Application Priority Data

Jul. 18, 1989 [EP] European Pat. Off. .............. 89113132

[51] Int. Cl.$^6$ ..................... C07K 5/00; C07K 7/00; C07K 16/00; C07K 17/00
[52] U.S. Cl. ..................... 530/317; 530/345; 530/322
[58] Field of Search ..................... 530/317, 322, 530/345

[56] References Cited

U.S. PATENT DOCUMENTS

| | | |
|---|---|---|
| 2,990,329 | 6/1961 | Philip et al. . |
| 3,067,099 | 12/1962 | McCormick et al. . |
| 4,239,751 | 12/1980 | Coronelli et al. . |
| 4,322,343 | 3/1982 | Debono . |
| 4,456,593 | 6/1984 | Herrin et al. . |
| 4,497,802 | 2/1985 | Debono . |
| 4,504,467 | 3/1985 | Molloy et al. . |
| 4,563,442 | 1/1986 | Clem et al. . |
| 4,639,433 | 1/1987 | Hunt et al. . |
| 4,643,987 | 2/1987 | Nagarajan et al. . |
| 4,698,327 | 10/1987 | Nagarajan et al. . |
| 5,438,117 | 8/1995 | Malabara et al. ............ 530/317 |

FOREIGN PATENT DOCUMENTS

| | | |
|---|---|---|
| 0276740 | 1/1988 | European Pat. Off. . |
| 0290922 | 5/1988 | European Pat. Off. . |

OTHER PUBLICATIONS

N. Pant et al., *J. Am. Chem. Soc.* 110, pp. 2002–2003(1988).
R. Nagarajan et al., *J. Chem. Soc., Che. Commun.*, pp. 1306–1307 (1988).
J. Weinstein et al., *Annals NY Academy of Sci.* vol. 471, pp. 321–323, (1986).

Kirk–Othmer, *Encyclopedia of Chemical Technology*, 3rd Edition, vol. 2, A Wiley Interscience Publication, pp. 809, (1978).
Gennaro, A.R., *Remington's Pharmaceutical Sciences* 18th ed., Pharmaceuticals Sciences, (1990), p. 757, 1163, 1214–1215.
Gilman, A.G., Rail, T.W., Nies, A.S., Taylor, P., Ed., *Goodman and Gilman's The Pharmacological Basis of Therapeutics* 8th ed., Pergamon Press, (1990), pp. 1018–1034.
Demain, A.L., Solomon, N.A., Ed., *Manual of Industrial Microbiology and Biotechnology*, American Soc. for Microbiology, (1986), pp. 24–26.
Budavari, S., O'Neil, M.J., Smith, A., Heckelman, P.E., Ed., *The Merck Index*, 11th ed., (1989), p. 1438, 1311, 1561.
Malabarba et al., *J. Antibiotics* vol. 37 No. 9 pp. 988–999, (1984).

*Primary Examiner*—Toni R. Scheiner
*Assistant Examiner*—Sheela J. Huff
*Attorney, Agent, or Firm*—Ruth E. Homan

[57] ABSTRACT

Pentapeptide antibiotics of the formula

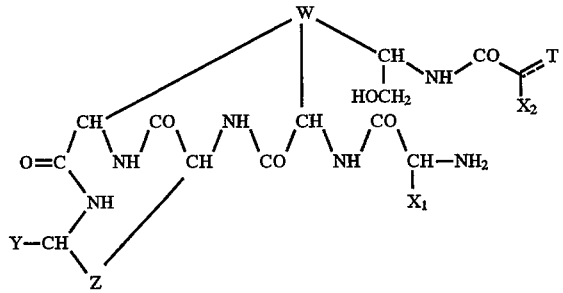

wherein W, Z, $X_1$, $X_2$ and T represent the relative portions of an antibiotic of the dalbaheptide group (glyccpeptide antibiotics), Y represents a carboxyacid group, a functional derivative of said carboxyacid group or a hydroxymethyl group. The invention includes the salts of the above represented pentapeptide antibiotics with acids or bases as well as their inner salts.

The compounds are obtained by reductive cleavage of the peptidic bond between the second and the third aminoacid of the seven aminoacid chain of dalbaheptides (glycopeptide antibiotics). The inventions concerns also the reductive cleavage process which implies using an alkali metal borohydride as the reagent. The compounds show antibacterial activity against staphylococcal and streptococcal strains.

14 Claims, No Drawings

PENTAPEPTIDE ANTIBIOTICS

This is a division of application Ser. No. 08/440,868, filed May. 15, 1995, which is a continuation of application Ser. No. 08/298,237, filed Aug. 30, 1994, now abandoned, which is a continuation of application Ser. No. 08/122,820, filed Sep. 17, 1993, now abandoned, which is a continuation of application Ser. No. 07/961,213, filed Oct. 15, 1992, now abandoned, which is a continuation of application Ser. No. 07/842,799, filed Feb. 27, 1992, now abandoned, which is a continuation of application Ser. No. 07/552,275, filed Jul. 12, 1990, now abandoned, which is herein incorporated by reference.

This invention concerns pentapeptide antibiotics deriving from dalbaheptide antibiotics of the formula

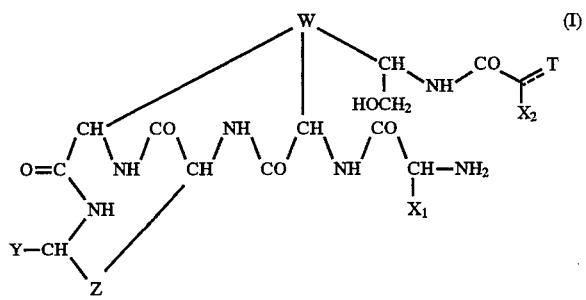

wherein W, Z, $X_1$, $X_2$ and T represent the relative portions of an antibiotic of the dalbaheptide group, Y represents a carboxyacid group, a functional derivative of said carboxyacid group or a hydroxymethyl group. The invention includes the salts of the above represented pentapeptide antibiotics with acids or bases as well as their inner salts.

A further object of this invention is a reductive cleavage process for producing the pentapeptide antibiotics from the corresponding dalbaheptide precursors.

With the term dalbaheptide are defined all antibiotic substances having in common a highly modified linear heptapeptidic structure made up of seven amino acids, five of which are constantly aryl- and arylmethylaminoacids, said structure being determinant of a common mechanism of action, i.e. the specific complexation with the D-alanyl-D-alanine terminus of one or more intermediates of the cell wall synthesis which leads to cell disruption (see also: Parenti, F. and Cavalleri, B. "Novel glycopeptide antibiotics of the dalbaheptide group". Drugs of the future, Vol. 15 (1):57–72 (1990)). The dalbaheptide antibiotics which are the precursors of the pentapeptide antibiotics of this invention can be represented conventionally with the following general structure wherein W, Z, $X_1$, $X_2$ and T have the same meanings as above and Y represents a carboxyacid group or a functional derivative thereof. The formula (II) includes the salts of dalbaheptide antibiotics with acids and bases as well as their inner salts.

According to this invention, the pentapeptide antibiotics of formula (I) can be obtained by reductive cleavage of the peptidic bond between the second and third amino acid (starting from the right) of the seven amino acids chain of the dalbaheptide antibiotics of formula (II).

In the general structure represented by the formula (II), the above mentioned five fundamental aryl- and arylmethyl amino acids are those linked with the groups Z and W. Apart from slight differences in the substitutions on the respective aryl portion, the five aryl- and arylmethyl amino acids are substantially common to all members of the dalbaheptide antibiotics group, while the different type and structure of the two remaining amino acid portions which bear the substituents $X_1$ and $X_2$ allow a further classification of the dalbaheptides so far known into four different sub-groups, each of which is referred, for practical reasons, to a well known antibiotic of the group that, in the previous scientific literature, has been generally identified as glycopeptide antibiotics.

Said four sub-groups can be defined respectively as ristocetin-type, vancomycin-type, avoparcin-type and synmonicin-type antibiotics.

According to the terms and definitions of this specification, the dalbaheptide antibiotics as well as the four sub-groups into which they are presently classified, includes both products produced as metabolites of microbial strains, as well as semisynthetic derivatives thereof. The fermentation products generally bear sugar moieties conjugated with the hydroxy groups positioned on the aryl or arylmethyl portions of the five fundamental amino acids, or on the $X_1$ and/or $X_2$ moieties when they contain hydroxylated aromatic ring moieties. In a few cases, one phenolic hydroxy function may be esterified with a sulfuric acid group. In the fermentation products the function represented by the symbol Y generally is a carboxy acid or a lower alkyl carboxyester, while the symbol T, in general, represents an amino, a lower alkyl amino (e.g. methylamino) or a tri(lower alkyl) ammonium function, e.g. (trimethylammonio).

The semisynthetic derivatives described in the patents and scientific literature are, for instance, products deriving from complete or partial hydrolysis of the sugar portions, thus having free hydroxy groups on the aryl or the arylmethyl portions, products deriving from the elimination of the benzylic hydroxy group on the arylmethyl portions, products deriving from the introduction of specific sugar moieties or aliphatic or alicyclic groups on a phenolic hydroxy function (see, for instance, ref. 66), products deriving from the

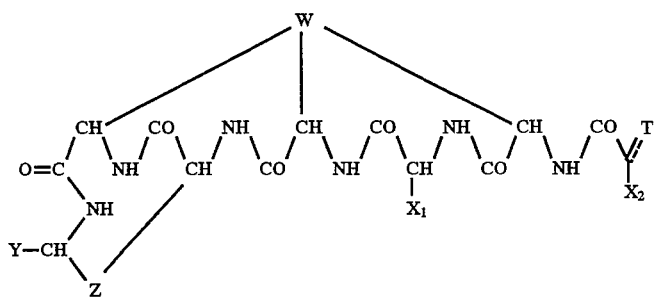

modifications of the carboxylic moiety Y to form functional derivatives thereof, e.g. esters, amide or hydrazide derivatives or products deriving from the modification of the portion T yielding various mono or di-substituted aminic rests (e.g. by alkylation or acylation) or resulting in a deamination or a substitution by a hydroxy, oxo or oxyimino function or products deriving from the acylation of the aminic groups of the amino sugar moieties, or products resulting from the dehalogenation of the aryl moieties originally containing halo substituents or products deriving from the introduction of halo (preferably chloro and bromo) substituents on the aryl moieties. Said semisynthetic derivatives may contain more than one of the above mentioned modifications of the basic structure of the natural products.

According to a more specific representation of most of the dalbaheptide antibiotics so far known, the structure of which has been determined (which is not limiting the scope of this invention), the symbols W and Z in the formula (II) above and in the formula (I) of the pentapeptides deriving therefrom can respectively represent the following partial structures:

W =

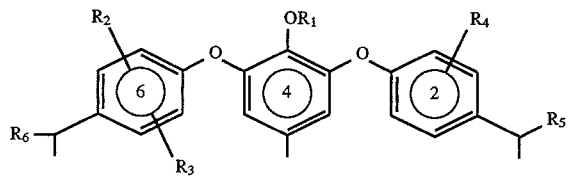

wherein $R_1$ is hydrogen, a sugar moiety, an aliphatic or alicyclic hydrocarbon group. $R_2$, $R_3$ and $R_4$, are each independently, hydrogen or halogen, preferably chloro or bromo, and are most preferably in the ortho position with respect to the ether bond. $R_5$ and $R_6$ are each independently hydrogen, or a group $OR_7$ wherein $R_7$ is hydrogen or a sugar moiety. As shown in formula (II) above, the group W is simultaneously linked to the second, fourth and sixth amino acid (starting from the right) group of the heptapeptidic chain of dalbaheptides;

Z =

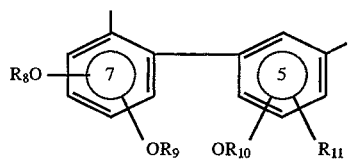

wherein the groups $OR_8$ and $OR_9$, preferably, are respectively in the para and ortho position with respect to the bond connecting the two phenyl rings and the radical $R_8$ and $R_9$ each independently represents hydrogen or a sugar moiety; most preferably $R_8$ is hydrogen. The group $OR_{10}$ is, preferably, in the position ortho with respect to the bond connecting the two phenyl rings and the radical $R_{10}$ represent hydrogen or a sugar moiety. The group $R_{11}$ is, preferably, in the position meta with respect to the bond connecting the two phenyl rings and represent hydrogen or halogen, most preferably, hydrogen or chloro. As shown in formula (II) above, the group Z is linked to the fifth and seventh amino acid (starting from the right) group of the heptapeptidic chain of dalbaheptides.

The meanings of the symbols $X_1$ and $X_2$ which permit the differentiation of the so far known dalbaheptide antibiotics into four sub-groups are respectively the following:

$X_1$ represents a phenyl or a benzyl group wherein the phenyl ring may optionally Dear one or two substituents selected from halogen, preferably chloro, lower alkyl, preferably methyl, and hydroxy wherein the hydroxy group can be optionally conjugated with a sugar moiety through an acetalic bond or esterified with a sulfuric acid residue, or it may also represent a $(C_1-C_2)$ aliphatic group substituted with a carboxylic or carboxamide function, a thiomethyl or a methylsulfinyl group.

$X_2$ represents a phenyl group which may optionally bear one or two substituents selected from halogen, preferably chloro, lower alkyl, preferably methyl, and hydroxy wherein the hydroxy group can be optionally conjugated with a sugar moiety through an acetalic bond, or it may represent a $(C_1-C_4)$ aliphatic group, preferably methyl or isobutyl.

$X_1$ and $X_2$ taken together may also represent a oxybis (phenylene) group where one or both phenyl rings may optionally be substituted as indicated above.

According to a more specific representation of most of the dalbaheptide antibiotics of formula (II) above so far known (including their semisynthetic derivatives) and of the pentapeptides of formula (I) of this invention driving therefrom, the symbol T, preferably, identifies an amino group wherein one or both hydrogen atoms may optionally be substituted by an alkyl radical of 1 to 12 carbon atoms which, in turn, can optionally bear one or more substituents, by a $(C_4-C_7)$ cycloalkyl by an acyl radical or by a suitable protecting group of the amino function or it may also represent a tri(lower alkyl)ammonium radical, whose positive charge is neutralized by an anion deriving from either a strong acid or an internal acid function, e.g. a carboxylate anion deriving from the carboxyacid moiety represented by the symbol Y. In some cases T may also represent hydrogen (e.g. teicoplanin semisynthetic derivatives) or a hydroxy, oxo or oxymino group (e.g. ristocetin derivatives). Accordingly, when T is a divalent radical the dotted line in both formula (I) and formula (II) represent an additional bond.

The symbol Y represents a carboxy group, a functional derivative thereof such as a carboxyester, a carboxamide, a carbohydrazide group or a hydroxymethyl group. This definition includes the naturally occurring lower alkyl esters as well as the esters formed by reaction of the carboxylic function with alcohols, e.g. aliphatic alcohols bearing substituents in the aliphatic chain, and includes also a wide series of substituted amides which are formed by reaction of the carboxy group with aliphatic, cycloaliphatic and heterocyclic amines. In particular the aliphatic amine may contain substituents on the aliphatic chain such as amino, lower alkylamino, di-lower alkylamino, hydroxy, lower alkoxy, carboxy, carbamyl, substituted carbamyl and the like.

The meaning of hydroxymethyl for Y in the pentapeptide compounds of formula (I) may result from the concomitant reduction of the lower alkyl ester function represented by the symbol Y in the dalbaheptide precursors of formula (II) during the reductive cleavage process of this invention.

The salts of the end compounds of formula (I) and starting compounds of formula (II) can be those deriving from the salification with an acid of the basic functions of the molecule, e.g., in the end compounds of formula (I), the amino function resulting from the reductive cleavage of the peptidic bond between the second and third amino acid of the dalbaheptide peptidic chain, or, in both the starting materials and end compounds, the amino function identified by the symbol T, or an amino function contained as substituent in the carboxyester, carboxamide or carbohydrazide moiety represented by the symbol Y or in a sugar moiety (e.g. vancomycin, avoparcin). Alternatively, the salts may be formed through salification of the carboxylic acid function represented by the symbol Y, or an acidic function contained as substituent in the carboxyester or carboxamide moiety or any acidic function which may be present in any other portion of the molecule, with an appropriate base. The inner salts are those formed through internal salification in the cases of simultaneous presence of basic (e.g. aminic) and acid (e.g. carboxylic) functions of sufficient strength in the dalbaheptide precursor and/or the pentapeptide end compounds.

In the dalbaheptide antibiotics, as well as in the pentapeptide derivatives resulting therefrom according to this invention, the sugar moieties which can be linked to the hydroxy groups are either mono-or polysaccharides which can be acetylated or methylated in one of the hydroxylic groups or deoxygenated in one or two positions and may bear carboxylic or amino substituents which can be acylated, for instance, by aliphatic acid radicals. Specific sugar moieties can be introduced through chemical or microbiological reactions on dalbaheptide substrates having free hydroxy groups on the aromatic rings.

Typical examples of unsubstituted monosaccharide moieties linked to the hydroxy groups of the basic dalbaheptide structure include both hexoses and pentoses such as, for instance: glucose (e.g. actaplanin $B_2$), galactose (e.g. antibiotic A 41030C), mannose (e.g. teicoplanin $A_2$), fucose (e.g. antibiotic A 35512 B), rhamnose (e.g. avoparcin) and acetyl mannose (e.g. parvodicin $C_3$).

Typical examples of carboxy or amino substituted monosaccharide moieties linked to the hydroxy groups include N-acetyl glucosamine (e.g. teicoplanin $A_2$ complex), N-($C_9$–$C_{12}$) aliphatic acyl glucosamine (e.g. teicoplanin $A_2$ complex), ristosamine (e.g. ristocetin A), actinosamine (e.g. actinoidin A), N-($C_9$–$C_{12}$)aliphatic acyl-2-amino-2-deoxyglucuronic acid (e.g. ardacins).

Typical examples of polysaccharide moieties may contain both unsubstituted and carboxy or amino substituted sugars units such as glucose (e.g. actaplanin A), mannose (e.g. ristocetin A) (e.g. ristocetin A), rhamnose (e.g. ristocetin B), olivose (e.g. orienticin B), vancosamine (e.g. vancomycin) epi-vancosamine (e.g. orienticin A, C and D), acosamine, (e.g. actinoidin), and ristosamine (e.g. avoparcin), linked with at least another sugar unit. In the dalbaheptides so far known and whose structure have been determined polysaccharides containing up to four sugar units have been identified.

The characteristics which allow a further classification of the so far known dalbaheptides into four-sub-groups are in no way limiting the scope of this invention in that new natural products and derivatives thereof falling into the general classification of dalbaheptide antibiotics can be obtained and identified which can be converted to pentapeptides of formula I according to the process of this invention involving reductive cleavage of the amidic bond between the second and third aminoacid of the seven amino acid chain of the starting dalbaheptide. However, for a more precise identification of representative starting compounds that can be used according to this invention for obtaining the corresponding pentapeptides of formula (I), in the following is given a further detailed description of the four sub-groups mentioned above and of the corresponding pentapeptide antibiotics which can be obtained therefrom according to a preferred embodiment of this invention.

Referring to the formula II above, the sub-group identified as ristocetin-type dalbaheptides is characterized by the fact that the symbols $X_1$ and $X_2$ taken together represent an oxybis(phenylene) group wherein one or both phenyl rings may optionally bear one or two substituent selected from halogen, preferably chloro, lower alkyl, preferably methyl, and hydroxy wherein the hydroxy group can be optionally conjugated with a sugar moiety through an acetalic bond or esterified with a sulfuric acid residue.

Other dalbaheptide antibiotics which can be assigned to this sub-group include the following: actaplanin (ref. 7, 8), teicoplanin (ref. 9, 10, 11), antibiotic A 35512 (ref. 12, 13), antibiotic A 41030 (ref. 14, 15), antibiotic A 47934 (ref. 16, 17), ardacin A, B, C (ref. 18, 19, 20), antibiotic A 40926 (ref. 21, 22, 23), kibdelin (ref. 24), parvodicin (ref. 25), and antibiotic UK 68597 (ref. 26).

The semisynthetic derivatives of the above mentioned natural products are also included in this sub-group. See, for instance, the aglycone and pseudoaglycones of ardacins (ref. 27) and the derivatives thereof wherein Y is a carboxamide or a carbohydrazide group (ref. 28); the aglycone and pseudoaglycone of parvodicin (ref. 29); the hydrolysis products of actaplanins (ref. 30); the conversion products of the first amino acid moiety of ristocetin A, antibiotic A 35512, A 41030 and A 47934 to the corresponding keto-analogs (ref. 31 and 32); the acylation derivatives of ristocetin, actaplanin and their pseudoaglycons (ref. 33), the bromine analogs of actaplanin (ref. 34); the aromatic aldehyde derivatives of ristocetin (ref. 35); the derivatives of teicoplanin and antibiotic A 40926 which are more specifically considered below.

Accordingly, one of the objects of this invention consists in the pentapeptide antibiotics deriving from the ristocetin-type dalbaheptides which can be generally represented through formula (I) above where W, Z, T and Y are defined as above, $X_1$ and $X_2$ are as specifically defined for the identification of the ritocetin-type dalbaheptides sub-group.

For example, ristocetin A (ref. 1, 2) has the following structure formula:

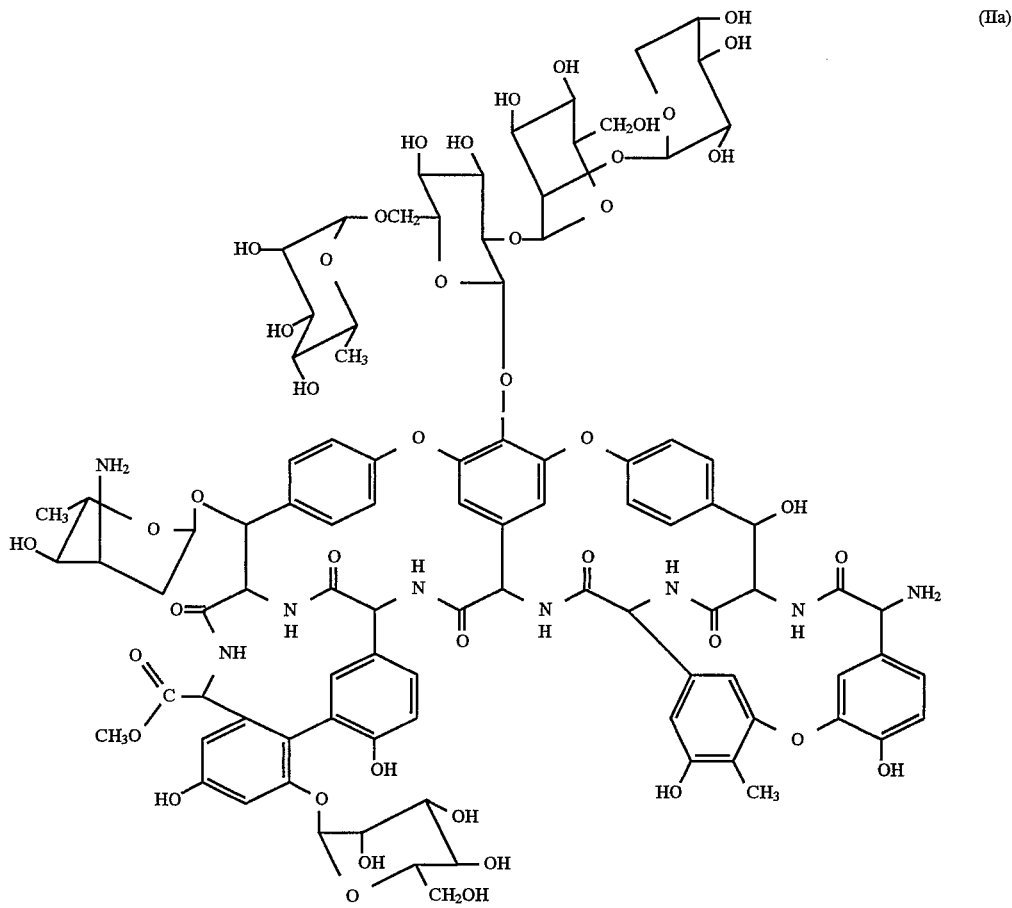

(IIa)

Referring to the symbols utilized in formula (II) above and to the groups Y, W, Z, $X_1$, $X_2$ and T, it can be seen that, in this case, Y corresponds to carboxymethyl, the groups Z and W are as specified above, with $R_2$, $R_3$ and $R_4$ all representing hydrogen and $R_1$ representing a four units sugar moiety wherein D-glucose is the member conjugated with the hydroxy group, the other units being L-rhamnose, D-mannose and D-arabinose, respectively. The symbol $R_5$ is a hydroxy group. The symbol $R_6$ is a hydroxy group conjugated with L-ristosamine. The symbol $OR_8$ is a hydroxy group. The symbol $OR_9$ is a hydroxy group conjugated with a D-mannose unit. The symbol $OR_{10}$ is a hydroxy group. The symbol $R_{11}$ is hydrogen. The symbols $X_1$ and $X_2$ taken together represents a oxybis(phenylene) radical linked to the first and third amino acid of the seven amino acids chain wherein the first (starting from the right) phenyl portion bears a hydroxy substituent and the second phenyl portion bears a hydroxy and a methyl group respectively as substituents. T represent an amino group.

Ristocetin B (ref. 1,2) is also known as well as the aglycone, pseudoaglycones and aglycone acid of the ristocetins (ref. 3,4,5,6), the semisynthetic derivatives of the aglycone, wherein the amino group represented by the symbol T is replaced by hydroxy, oxo, oximino and acetylamino (ref. 82), and the acyl derivatives mentioned above (ref. 33).

By applying the reductive cleavage process of this invention to ristocetin A, the corresponding derivative of formula Ia is obtained wherein Y is hydroxymethyl

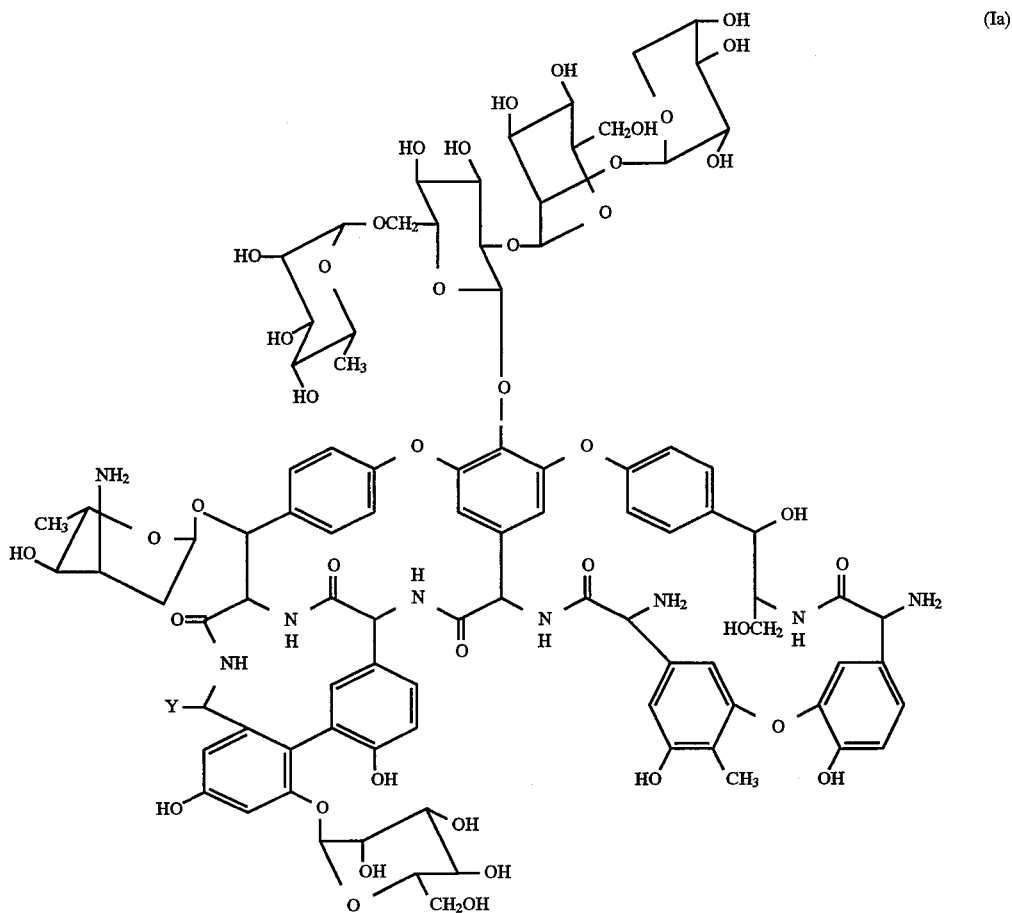

(Ia)

Under the current reaction conditions for carrying out said reductive cleavage process the carboxymethyl ester function of ristocetin A is reduced to the corresponding alcohol. On the contrary, by applying the same conditions to the ristocetin aglycone acid, (i.e.: formula (IIa) wherein the sugar moieties are replaced by hydrogen atoms and the carboxy ester group is hydrolyzed), the corresponding compound of formula (Ia) is obtained wherein Y is a carboxylic group and all sugar moieties are replaced by hydrogen atoms. This compound can be used as an intermediate for obtaining an end compound of formula (Ia) wherein the carboxylic group is esterified. The esterification can be carried out according to methods known in the art, for instance, according to Intern. Appln. Publ. No. 86/00075.

A particular group of compounds which can be assigned to the ristocetin-type dalbaheptides includes the teicoplanin $A_2$ complex, its main components (ref. 9) and related substances (ref. 36, 37) as well as the aglycone, pseudoaglycones (ref. 38, 39, 40) and the semisynthetic derivatives thereof.

Teicoplanin $A_2$ complex main components and related substances as well as teicoplanin aglycone (L 17392, ref. 39), pseudoaglycones (L 17054=T-A3-1, and L 17046=T-A3-2, ref. 39) and most of the semisynthetic derivatives thereof can be represented by the following general formula (IIb):

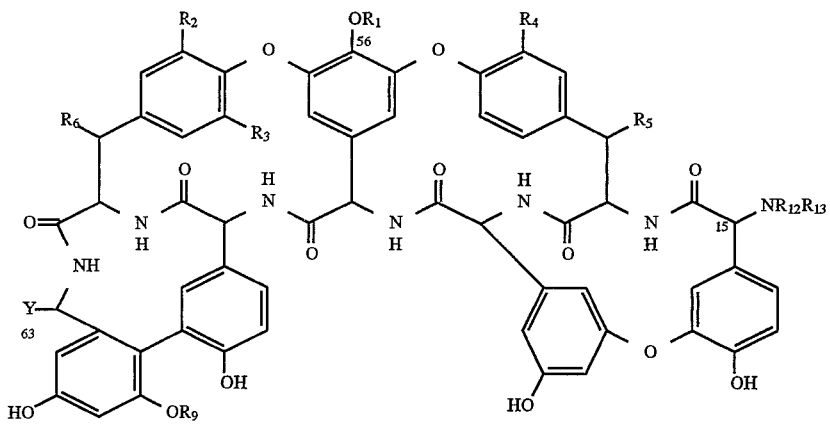

(IIb)

In particular, the main components of teicoplanin $A_2$ complex and the related substances are represented by the above formula (IIb) wherein $R_1$ is a N-($C_9$-$C_{12}$) aliphatic acyl-beta-glucosamine group, $R_3$ and $R_4$ are both chloro, $R_2$, $R_5$, $R_{12}$ and $R_{13}$ are hydrogen, $R_6$ is a group —$OR_7$ wherein $R_7$ represents a N-acetyl-beta-D-glycosaminyl group, $R_9$ is an alpha-D-mannosyl rest, Y is a carboxylic group.

More particularly, the ($C_9$-$C_{12}$) aliphatic acyl radicals which characterize the glucosamine moiety of teicoplanin $A_2$ main components and related substances so far described are the following (ref. 9, 11, 36, 37):Z-4-decenoyl, 8-methylnonanoyl, decanoyl, 8-methyldecanoyl, 9-methyldecanoyl, n-nonanoyl, 6-methyloctanoyl, 10-methylundecanoyl and dodecanoyl.

The aglycone and pseudoaglycones may also be represented by the above formula (IIb) wherein one or more of the symbols $R_1$, $R_7$ and $R_9$ are representing hydrogen with the proviso that $R_7$ is hydrogen only if $R_1$ is hydrogen.

The chemical structures of the semisynthetic derivatives which are particularly interesting for their biological activity have the same basic structure of the teicoplanin main components, the related substances, aglycone and pseudoaglycone with the modifications of either/both the $C^{63}$ carboxy group or/and the amino group on the $C^{15}$. In particular, the $C^{63}$ carboxy group corresponding to the symbol Y in the formula (IIb) above has been modified to the corresponding esters according to Int. Appl. Publ. No. WO 86/00075 and carboxamide group $CONR_{14}R_{15}$ according to the meanings set forth respectively in the European Pat. Appln. Publ. No. 218099, Int. Pat. Appln. Publ. No. WO 88/06600, and Int. Pat. Appln. Ser. No. PCT/EP90/00400 and European Pat. Appln. Publ. No. 370283.

In the semisynthetic derivatives, the amino group $NR_{12}R_{13}$ on the $C^{15}$ identifies an amino radical modified by reaction with protecting groups or by conversion into the corresponding alkylamino or dialkylamino group wherein the alkyl portion(s) can bear further substituents according to European Pat. Appln. Publ. Nos. 276740, 351597, 351684 and 351685. Teicoplanin derivatives presenting modifications in both $C^{63}$ carboxylic group and amino group on the $C^{15}$ and processes for their manufacture have been described in European Pat. Appln. Publ. Nos. 352538 and 370283.

Other semisynthetic teicoplanin derivatives described in the prior art include the esters and hydrazides of the $C^{63}$ carboxy group (ref. 41 and 42), the de-acetyl glucosaminyl-deoxy teicoplanins (ref. 43) and the corresponding $C^{63}$ carboxyamides (ref. 44) the mono and di-dechloroderivatives of teicoplanin (ref. 45), and the $O^{56}$ alkyl and cycloalkyl derivatives of teicoplanin aglycone and pseudoaglycones of teicoplanin (ref. 46 and 97).

All the above mentioned semisynthetic teicoplanins can be represented by the formula (IIb) above with the attribution of the appropriate meanings to the symbols $R_1$, $R_2$, $R_3$, $R_4$, $R_5$, $R_6$, $R_7$, $R_9$, $R_{12}$, $R_{13}$ and Y.

A preferred embodiment of this invention, include the pentapeptide antibiotics of formula (Ib)

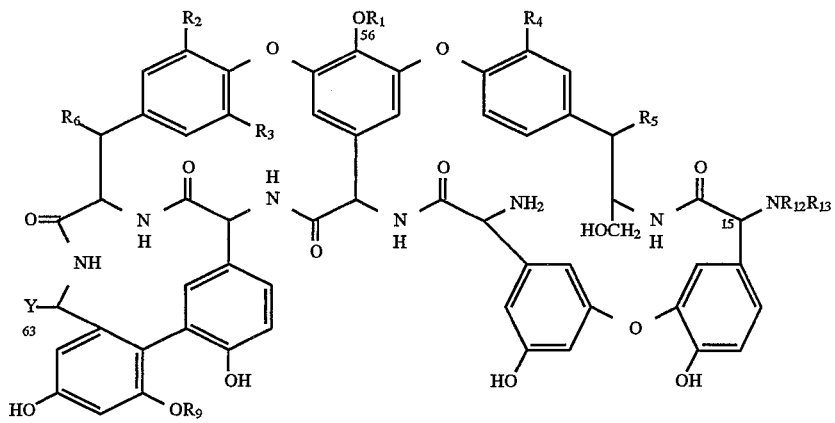

(Ib)

which can be obtained by reductive cleavage of the peptidic bond between the second and the third (starting from the right) amino acid of the seven amino acids chain of teicoplanin compounds represented in formula IIb above. The symbols $R_1$, $R_2$, $R_3$, $R_4$, $R_5$, $R_6$, $R_7$, $R_9$, $R_{12}$, $R_{13}$ and Y in the above formula (Ib) have the same meanings as those of the starting materials of the formula IIb with the proviso that when the symbol Y of the starting teicoplanin compound represents a carboxyester group, in the corresponding compound of formula (Ib) obtained through the reductive cleavage process of this invention, Y represents a hydroxymethyl group as it occurs with ristocetin.

A further particular group of compounds falling within the ristocetin-type dalbaheptides sub-group comprises antibiotic A 40926 complex and its main factors (ref. 21, 22, 23) as well as the aglycon (ref. 48), the mannosyl aglycon (ref. 47), the N-acylamino-deoxy-glycuronyl aglycones (ref. 48) and the deacyl derivatives (ref. 49). Also these compounds are suitable starting materials for conversion into the corresponding pentapeptide antibiotics of general formula (I) through the reductive cleavage process of this invention.

The dalbaheptide antibiotic sub-group identified as vancomycin-type dalbaheptides is characterized by the fact that (reference is made to formula II above) the symbol $X_1$ represents a ($C_1$-$C_2$)aliphatic group substituted with a carboxylic or carboxamide function and the symbol $X_2$ represents a ($C_1$-$C_4$)aliphatic group. In particular, in the most common examples of antibiotic substances falling within this sub-group, $X_1$ is a residue deriving from aspartic acid, aspargine or glutamine, while $X_2$ is a residue deriving from alanine or leucine.

Some vancomycin-type dalbaheptides (e.g. M43A, B and C, ref. 55) are further characterized by the fact that T represents a trimethylammonio group whose positive charge is neutralized by the carboxylate anion formed by the carboxylic group represented by the symbol Y.

Other dalbaheptide antibiotics which can be assigned to this sub-group include the following: OA-7653 (ref. 51, 52), A 51568 A and B (ref. 53, 54), orienticins (ref. 56, 57), eremomycin (ref. 58, 59, 60, 61), A 42867 (ref. 50, 62), A 82846 (ref. 63, 64), chloroorienticins (ref. 65), MM 47761 and MM 49721 (ref. 94), decaplanin (ref. 95), MM 45289 and MM 47756 (ref. 96).

The semisynthetic derivatives of the above mentioned natural products are included in this sub-group. See for instance: the variously glycosylated derivatives of the hydrolysis products of vancomycin, A 51568A and B and M 43D (ref. 66); the desvancosaminyl and des(vancosaminyl-O-glucosyl)-derivatives of vancomycin, A 51568A; A 51568B, M 43A and M 43B (ref. 67), the derivatives of A 82846 (ref. 93); the reaction products of the amino groups of some vancomycin-type dalbaheptides with aldehydes and ketones and the corresponding hydrogenation products (ref. 68, 69), the N-acyl derivatives of vancomycin-type antibiotics (ref. 70, 71), mono- and didechlorovancomycin (ref. 72) and the hydrolysis products of eremomycin (ref. 60).

Accordingly, one of the objects of this invention consists in the pentapeptide antibiotics deriving from the vancomycin-type dalbaheptides which can be generally represented through the formula (I) above where W, Z, T and Y are defined as above, $X_1$ and $X_2$ are as specifically defined for the identification of the vancomycin-type dalbaheptide sub-group.

For example vancomycin (ref. 2, 73, 74) has the following structure formula:

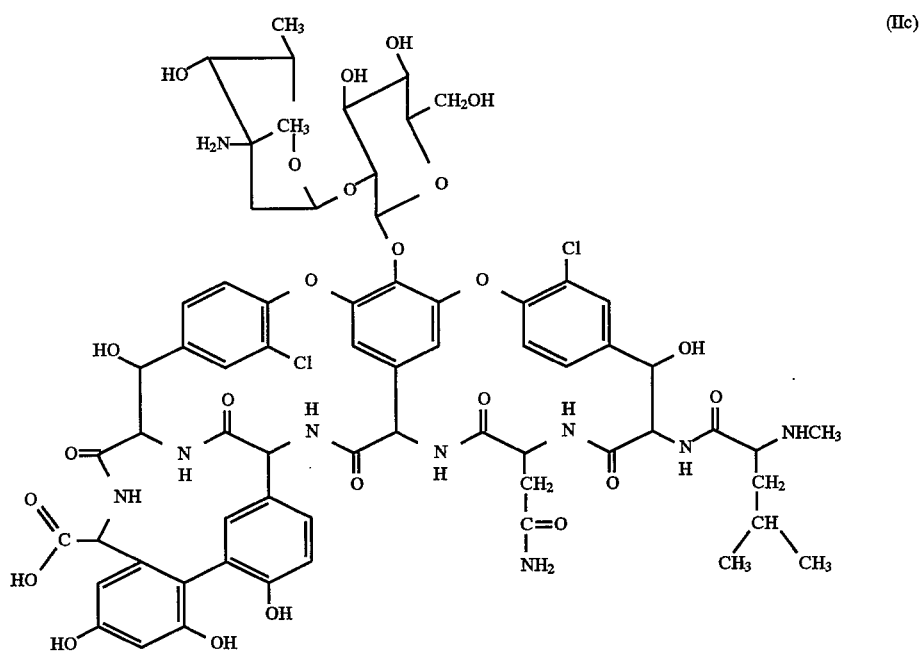

(IIc)

Referring to the symbols utilized in formula (II) above and the groups Y, Z, W, $X_1$, $X_2$, and T, it can be seen that in this case Y corresponds to a carboxy group, the groups Z and W are as specified above with $R_2$ representing hydrogen, $R_3$ and $R_4$ both representing chloro and $R_1$ representing a two units sugar moiety wherein D-glucose is the member conjugated with the phenolic hydroxy group, the other unit being vancosamine. The symbols $R_5$ and $R_6$ are hydroxy groups. Each of the symbols $OR_8$, $OR_9$ and $OR_{10}$ represent a hydroxy group. $R_{11}$ is hydrogen, $X_1$ is an aspargine residue —$CH_2CONH_2$ and $X_2$ is a leucine residue —$CH_2CH(CH_3)_2$. T is a methylamino group. In the vancomycin aglycone the two units sugar moiety is substituted by a hydrogen atom.

By applying the reductive cleavage process of this invention to vancomycin the corresponding pentapeptide antibiotic derivative of formula (Ic) is obtained:

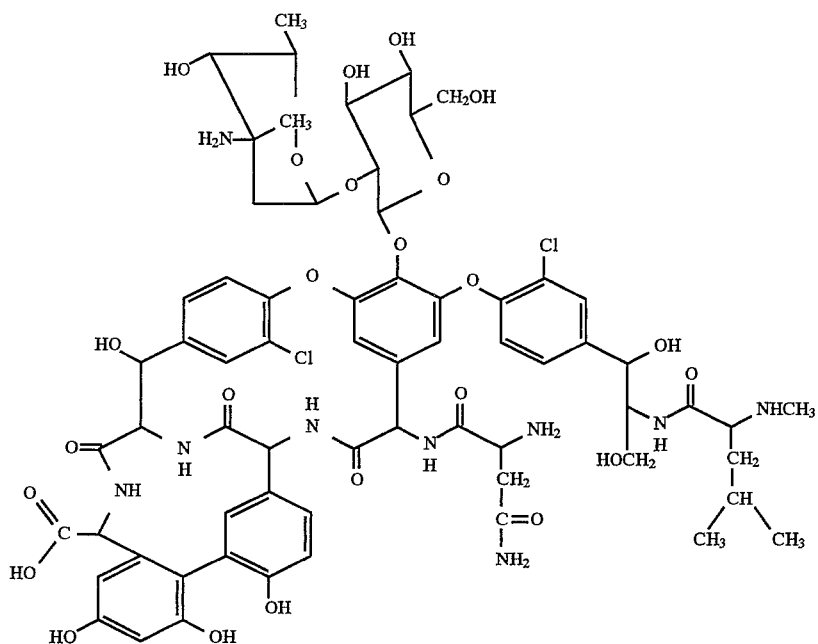
(Ic)

Analogously, the vancomycin aglycone yields the corresponding pentapeptide compound wherein the disaccharide moiety is replaced by a hydrogen atom.

The avoparcin-type dalbaheptide sub-group is characterized by the fact that the symbol $X_1$ in the general formula (II) represents a phenyl or benzyl group wherein the phenyl ring may optionally bear one or two substituents selected from hydroxy and halogen, preferably chloro, the symbol $X_2$ represents a phenyl group which may optionally bear one or two substituents selected from halogen, preferably chloro, and hydroxy which may optionally be conjugated with a sugar moiety (e.g. rhamnose).

Other dalbaheptide antibiotics which can be assigned to this group include the following: actinoidin A, B (ref. 1, 75, 76), chloropolysporin A, B, C (ref. 77, 78, 79), actinoidin A2 (ref. 80, 76) and helvecardin A, B (ref. 26), MM 47767, MM 55256 (ref. 92). Semisynthetic derivatives of avoparcin-type sub-group of dalbaheptide antibiotics are for instance the demannosyl chloropolysporin B derivatives, the chloropolysporin pseudoaglycone, the derhamnosyl alpha and beta avoparcin (ref. 81), the mannosyl aglycones of avoparcin (LL-AV290) and other derivatives wherein one or more sugar moieties are hydrolyzed (ref. 84).

Accordingly, one of the objects of this invention consists in the pentapeptide antibiotics deriving from the avoparcin-type dalbaheptides which can be generally represented through formula (I) above where W, Z, T and Y are defined as above, $X_1$ and $X_2$ are as specifically defined for the identification of the avoparcin-type dalbaheptide sub-group.

For example alpha and beta avoparcin (ref. 83, 84, 85) have the following structure formula:

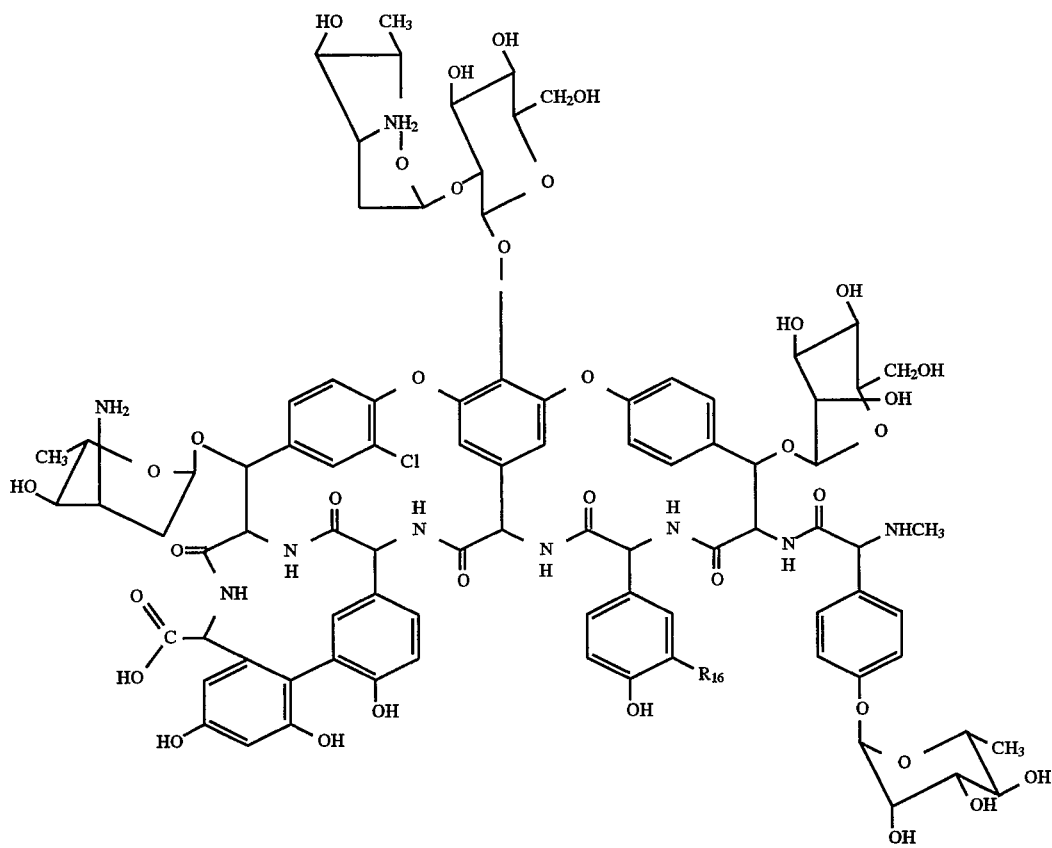

(IId)

wherein $R_{16}$ is hydrogen or chloro.

Referring to the symbols utilized in formula (II) above and to the groups Y, W, Z, $X_1$, $X_2$ and T, it can be seen that, in this case, Y corresponds to carboxy, the group Z and W are as specified above with $R_3$ representing chloro and $R_2$ and $R_4$ both representing hydrogen, $R_1$ being a two units sugar moiety wherein D-glucose is the member conjugated with the phenolic hydroxy group, the other unit being L-ristosamine. The symbol $R_5$ is a hydroxy group conjugated with a D-mannose unit. The symbol $R_6$ is a hydroxy group conjugated with L-ristosamine. The symbols $OR_8$, $OR_9$ and $OR_{10}$ each represents a hydroxy group. The symbol $R_{11}$ is hydrogen. The symbol $X_1$ is a phenyl group substituted with hydroxy and a radical $R_{16}$ which represents hydrogen in alpha-avoparcin and chloro in beta-avoparcin. The symbol $X_2$ is phenyl substituted with a hydroxy group conjugated with a rhamnose unit. T represent a methylamino group.

By applying the reductive cleavage process of this invention to beta- and alpha- avoparcin the corresponding pentapeptide antibiotic derivatives of formula (I d) are obtained.

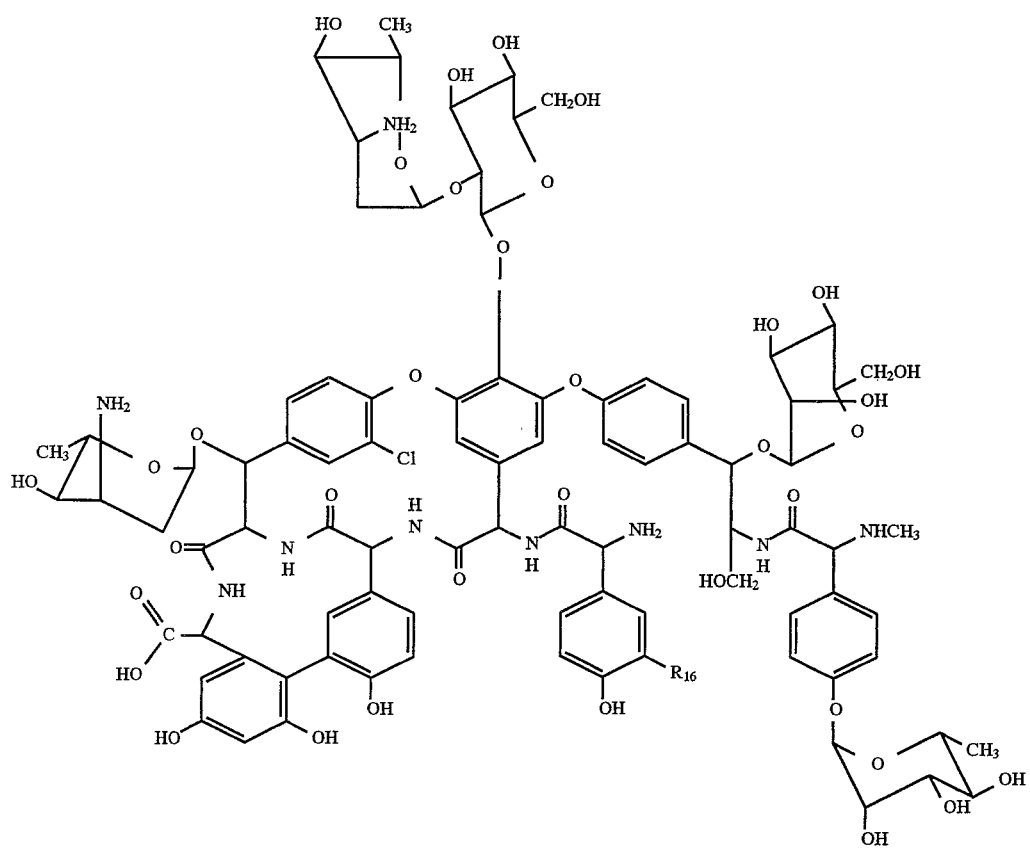
(Id)

wherein $R_{16}$ has the same meanings as above.

If the reductive cleavage process is applied to the dalbaheptide derivatives of formula (IId) wherein one or more sugar moieties are hydrolyzed, the corresponding pentapeptide compounds of formula (Id) are obtained.

The dalbaheptide antibiotics sub-group identified as synmonicin-type antibiotics is characterized by the fact that (reference is made to formula II above) the symbol $X_1$ represents a $C_2$ alkyl rest substituted on the terminal carbon with a thiomethyl or methylsulfinyl group, and the symbol $X_2$ represent a phenyl group bearing a hydroxy substituent which may be conjugated with a sugar moiety. Syrunonicin (CWI-785) complex, its components and some of its hydrolysis products (ref. 86, 87, 88) seem to be, for the moment, the only members of this sub-group.

Accordingly, one off the objects of this invention consists in the pentapeptide antibiotics derived from the synmonicin-type dalbaheptides which can be generally represented through formula (I) above where W, Z, T and Y are defined as above, $X_1$ and $X_2$ are as specifically defined for the identification of the synmonicin-type dalbaheptide sub-group.

For instance, synmonicin A and B have the following structure formula

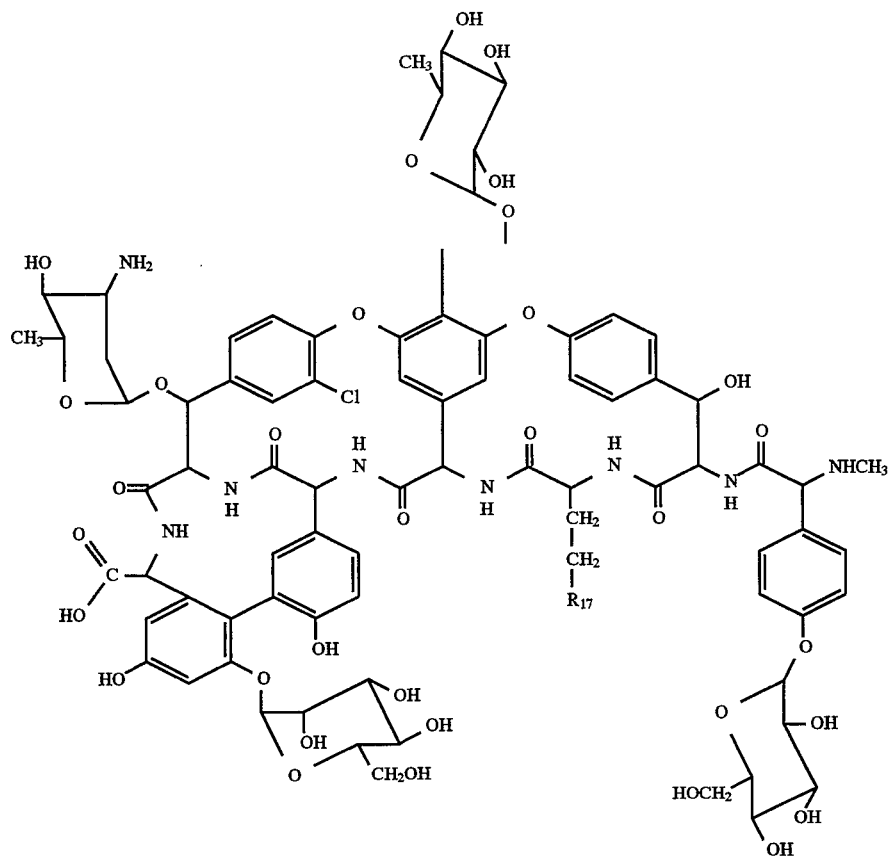

(IIe)

wherein $R_{17}$ is methylsulfinyl or thiomethyl.

Referring to the symbols utilized in formula (II) above and to the group Y, W, Z, $X_1$, $X_2$ and T, it can be seen that, in this case, Y corresponds to carboxy, the groups Z and W are as specified above, with $R_3$ representing chloro, $R_2$ and $R_4$ both representing hydrogen, and $R_1$ representing a rhamnose unit. The symbol $R_5$ is a hydroxy group. The symbol $R_6$ is a hydroxy group conjugated with a vancosamine unit. The symbol $OR_8$ is a hydroxy group. The symbol $OR_9$ is a hydroxy group conjugated with a mannose unit. The symbol $OR_{10}$ is a hydroxy group. The symbol $R_{11}$ is hydrogen. The symbol $X_1$ is an ethyl group substituted on the terminal carbon with thiomethyl (synmonicin B) or methylsulfinyl (syrunonicin A). The symbol $X_2$ is a phenyl group substituted with a hydroxy group conjugated with a glucose unit.

By applying the reductive cleavage process of this invention to synmonicin A and B the corresponding pentapeptide antibiotic derivatives of formula (Ie) are obtained

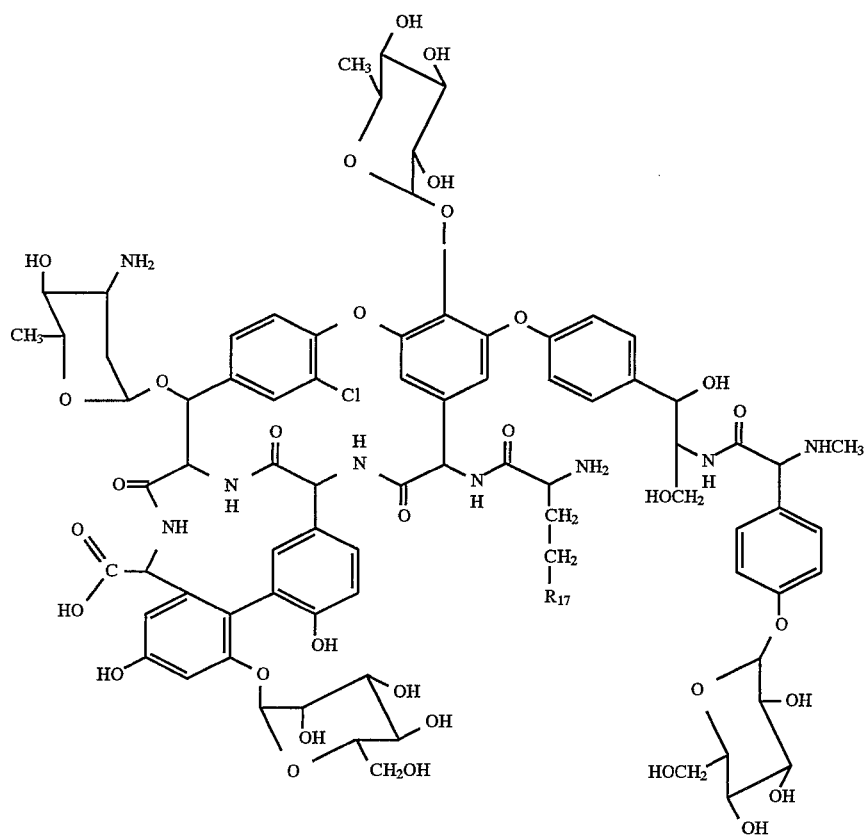

wherein R₁₇ has the same meanings as above.

If the reductive cleavage process is applied to the dalbaheptide derivatives of formula (IIe) wherein one or more sugar moieties are hydrolyzed, the corresponding pentapeptide compounds of formula (Ie) are obtained.

The pentapeptide antibiotic of this invention can be isolated as a free bases or as addition salts with acids or bases. Representative acid addition salts are those formed by reaction with both inorganic and organic acids, for example, hydrochloric, sulfuric, phosphoric, succinic, citric, lactic, maleic, fumaric, cholic, d-glutamic, d-camphoric, glutaric, phthalic, tartaric, methanesulfonic, benzenesulfonic, benzoic, salicylic, trifluroacetic acid and the like.

The salts with bases are those salts formed by reaction of an acid group of the pentapeptide antibiotic, e.g. a carboxylic or a sulfuric acid group, with a base such as, for instance, an alkali metal hydroxide or carbonate or an organic amine, such as mono-, di- or trialkyl-amine and the like.

The addition salts with pharmaceutically acceptable acids are particularly preferred.

The pentapeptide antibiotics of this inventions show antibacterial activity against staphylococcal and streptococcal strains such as *Staphylococcus aureus* Tour, *Staphylococcus epidermidis* ATCC 12228, *Streptococcus pyogenes* C 293, *Streptococcus pneumoniae* UC41, *Streptococcus faecalis* ATCC 7080, *Streptococcus mitis*. Although the activity of the pentapeptides is lower than that of their respective dalbaheptide precursors it is surprising that the drastic structural modification in the binding regions has not suppressed the antibacterial activity. In fact, it is known that the binding site responsible of the complexation with the D-alanyl-D-alanine terminus of the intermediates of the cell wall synthesis resides in the right hand part of the dalbaheptides molecules as it is shown in the literature of the field (ref. 89). A confirmation of these structural requirements is given by the inactivity of the hexapeptide products deriving from Edman degradation of vancomycin and aglucovancomycin (ref. 90).

The finding of an antimicrobial activity of the pentapeptide antibiotics of this invention is even more surprising if it is considered the result of the tests measuring their binding to the synthetic peptide analogue of the cell wall D-alanyl-D-alanine terminus, N,N'-diacetyl L-lysyl-D-alanyl-D-alanine. The tests carried out according to the differential UV assay (ref. 91) show that the pentapeptide do not bind to such analogue.

The antibiotic activity of the compounds of the invention is demonstrated in vitro by means of standard two-fold dilution tests in microtiter, using Difco TODD-HEWITT broth (*Strept. pyoqenes* and *Strept. pneumoniae*) or Oxoid ISO-SENSITEST broth (Staphylococci, *Strept. faecalis*). Broth cultures are diluted enough so that the final inoculum is about $10^4$ colony forming units/ml (CFU/ml). Minimal inhibitory concentration (MIC) is considered as the lowest concentration which shows no visible growth after 18–24 h incubation at 37° C. Some representative results are reported in the following TABLE I.

TABLE 1

In vitro activity of representative pentapeptide antibiotics
MIC (micrograms/ml)

| Pentapeptide Compound Example No. | STAPH. AUREUS TOUR | STAPH. EPIDERMIDIS ATCC 12228 | STREPT. PYOGENES C 203 | STREPT. PNEUMONIAE UC 41 | STREPT. FAECALIS ATCC 7080 | STREPT. MITIS 796 |
|---|---|---|---|---|---|---|
| 2 | 8 | 2 | 1 | 4 | 4 | 4 |
| 5 | 4 | 2 | 8 | 16 | 16 | 16 |
| 6 | 16 | 32 | 8 | — | 16 | — |
| 9 | 16 | — | 2 | 16 | — | — |

The pentapeptide derivatives of dalbaheptide antibiotics may be prepared according to a highly selective reductive cleavage process which implies concomitant splitting of the peptidic bond between the second and the third amino acid (starting from the right) of the seven amino acid chain of dalbaheptides and reduction of the carbonyl group of the second amino acid.

The procedure comprises submitting a dalbaheptide antibiotic as defined above in a hydroalcoholic medium to a reductive cleavage with an alkali metal borohydride, preferably selected from sodium borohydride, potassium borohydride and sodium cyanoborohydride at a temperature comprised between 0° C. and 40° C.

The hydroalcoholic medium is a mixture of $H_2O$ and a lower alkanol wherein the ratio $H_2O$/alcohol ranges between 40/60 and 90/10 (v/v), preferably between 60/40 (v/v) and 68/32 v/v, most preferably is 65/35 (v/v). Although the reaction occurs, in some cases, also in the presence of lower amounts of water, e.g. in mixtures $H_2O$/alcohol 30/70 or 20/80, in general, the reaction rate is very low when the ratio $H_2O$/alcohol is lower than 40/60.

Preferred lower alkyl alcohols are linear and branched ($C_1$–$C_4$) alkyl alcohols, among which the most preferred are ethanol and methanol.

In a particular preferred embodiment of the process of the invention a hydroalcoholic mixture $H_2O$/ethanol 65/35 (v/v) is used.

Sometimes, in particular cases, a small amount of a polar co-solvent can be added to completely dissolve the dalbaheptide starting material during the course of the reaction, e.g. N,N-dimethylformamide, 1,3-dimethyl-3,4,5,6-tetrahydro-2(1 H)-pyrimidone (DMPU), dimethylsulfoxide.

As alkali metal borohydride the sodium borohydride is the most preferred one. The suitable amount of alkali metal borohydride employed may vary depending on the particular dalbaheptide compound used as starting material, on the solvent used and on the temperature of the reaction, but it is advisable to use an amount of alkali metal borohydride in a large excess over the stoichiometric requirement in such a way that the pH of the reaction mixture is alkaline, preferably between pH 8 and 10. Anyway, in general, the molar ratio between the alkali metal borohydride and the antibiotic starting material is comprised between 50 and 300.

The reaction temperature may vary considerably depending on the specific starting materials and reaction conditions. In general, it is preferred to conduct the reaction at a temperature between 0° and 40° C., more preferably at room temperature. Also the reaction time may vary considerably depending on the other reaction parameters. In general, the reaction is completed in about 10–48 hours. In any case, the reaction course is monitored by TLC or, preferably, by HPLC according to methods known in the art. On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further separations and purifications by column chromatography, when needed.

After the reaction is completed, in most cases, but not necessarily in all cases, depending on the starting dalbaheptide, a clear solution is formed; then the excess of the alkali metal borohydride is eliminated by adding a suitable amount of an acid, for example, a ($C_1$–$C_4$)alkyl organic acid, a ($C_1$–$C_6$) alkyl sulfonic acid, an aryl sulfonic acid and the like, dissolved in a polar protic solvent such as, for example a ($C_1$–$C_4$) alkyl alcohol.

In order to better emphasize the striking aspect of the process of the invention it is necessary to underline that in general, the weakly basic conditions (pH 8–10) obtained with an aqueous solution of sodium borohydride are not sufficient to promote the hydrolysis of an amidic bond, but, the high selectivity of the reaction, which involves one peptidic bond in the heptapeptide chain, implies an unexpected activation of this linkage. In a particular case as described above, when the starting material contains an ester group, for instance a methyl ester group (see ristocetin A), said group is reduced to hydroxymethyl, before the reductive cleavage of the peptide bond is completed.

In a further aspect of the present invention, the sugar moieties of the compounds of formula (I) which are obtained through the reductive cleavage process of this invention may be successively removed by selective acid hydrolysis to transform them into other compounds of formula (I) wherein the sugar moieties are totally or partially replaced by hydrogen atoms. For example, a pentapeptide compound prepared with the reductive cleavage process of the invention starting from a teicoplanin compound of formula (IIb) wherein $R_1$, $R_7$ and $R_9$ each represents a sugar moiety as above defined, can be transformed into the corresponding pentapeptide compound of formula (Ib) wherein $R_7$ and $R_9$ are as above and $R_1$ is hydrogen by means of controlled acid hydrolysis in a strong concentrated aqueous organic acid.

The concentrated organic acid, in this case, is preferably aqueous trifluoroacetic acid at a concentration between 75% and 95%, and the reaction temperature is preferably between 10° C. and 50° C. The preferred hydrolysis conditions are represented by about 90% trifluoroacetic acid at room temperature.

The reaction time varies depending on the other specific reaction parameters but, in any case, the reaction may be monitored by TLC or preferably HPLC techniques.

An analogous selective hydrolysis is reported in European Patent Application Publication No. 146822. Similarly, another pentapeptide compound prepared with the process of the invention starting from a teicoplanin compound of formula (IIb) wherein $R_1$, $R_7$ and $R_9$ each represents a sugar moiety as above defined or $R_1$ represents hydrogen and $R_7$ and $R_9$ represent sugar moieties as above defined can be transformed into the corresponding pentapeptide compound of formula (Ib) wherein $R_1$ and $R_9$ represent hydrogen and $R_7$ represents a sugar moiety as defined above by means of a selective hydrolysis with a strong acid in the presence of a polar aprotic solvent selected from ethers, ketones, and mixture thereof which are liquid at room temperature.

Preferred hydrolysis conditions are in this case represented by the use of a concentrated mineral acid in the presence of an ether such as dimethoxyethane at room temperature. Also in this case, the reaction course may be monitored by TLC or preferably, HPLC. An analogous selective hydrolysis procedure is reported in European Patent Application Publication No. 175100.

Furthermore, a pentapeptide compound prepared with the process of the invention starting from a teicoplanin compound of formula (IIb) wherein $R_1$, $R_7$ and $R_9$ represent sugar moieties as defined above, or a compound of formula (IIb) wherein $R_1$ and $R_9$ represent hydrogen, and $R_7$ represents a sugar moiety as above defined may be transformed into the corresponding pentapeptide compound of formula (Ib) wherein $R_1$, $R_7$ and $R_9$ represent hydrogen atoms by means of a selective hydrolysis in an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl-substituted lower alkanols wherein the phenyl moiety may optionally carry $(C_1-C_4)$alkyl, $(C_1-C_4)$ alkoxy or halo groups which at the reaction temperature are liquids, slightly mixable with water, and beta-polyhalogenated lower alkanols, which at the reaction temperature are liquids, in the presence of a strong acid, compatible with the solvent, selected from strong mineral acids, strong organic acids and strong acid cation exchanger resins in the hydrogen form and at a temperature between 20° C. and 100° C. In this case, the preferred hydrolysis conditions are represented by the use of a mineral acid, such as hydrochloric acid, in an haloalkanol such as trifluoroethanol, at a temperature between 65° C. and 85° C. Analogous selective hydrolysis conditions on a similar substrate are described in European Patent Application Publication No. 146053. Alternatively, the hydrolysis of the sugar moieties may be carried out in aprotic polar solvent (e.g. dimethylsulfoxide) with a strong acid following the procedure disclosed in the European Pat. Appln. Publ. 376042.

The pentapetide compounds resulting from the reductive cleavage process or from the hydrolysis procedures described above can be directly isolated in the form of free bases or salts with acid or bases as described above. In particular, when the end compound is obtained by hydrolytic degradation of the sugar moiety(ies) of another pentapeptide of formula (I), it may be isolated as a salt of the same acid employed for the selective hydrolysis. In some cases, when the starting dalbaheptide has no sugar moiety and the symbol T identifies an amino (e.g. teicoplanin aglycone) or alkylamino group protected by acylation with an alkanoyl group, or alkoxycarbonyl group, or a benzyloxycarbonyl rest, the reductive cleavage according to the conditions described above does not occur or gives very low yields. In such cases, the reductive cleavage reaction can be carried out on the deprotected dalbaheptide according to the general conditions described above and the protecting acyl group, if desired, can be successively introduced by reacting the resulting pentapeptide with the appropriate acylating reactant. In those cases where the acylation conditions involve reaction of both amino groups of the pentapeptide, the desired N-acyl derivative can be obtained through selective deacylation procedures known in the art.

EXPERIMENTAL SECTION

In Table II for each group of pentapeptide compounds the raw formula, the equivalent and the molecular weight are reported.

Acid-base titrations were carried out under the following conditions: the sample was dissolved in a mixture methyl cellosolve/$H_2O$ 4/1, then an excess of 0.01M HCl in the same solvent mixture was added and the resulting solution was titrated with 0.01N NaOH.

Table III shows the $^1H$ NMR spectra recorded with a 24 mg solution of the proper pentapeptide product in 0.5 mL of DMSO-$d_6$ at 303° K. on a BRUKER AM 500 NMR-spectrometer equipped with an ASPECT 3000 computer, using $(CH_3)_4Si$ (delta 0.00 ppm) as internal reference. In particular, in Table III are reported only the significative delta concerning the portions of the new $CH_2OH$ group as the assignments of the other protons are already well known and there are no other significant chemical modifications in the pentapeptide molecule.

FAB-MS positive ion spectra (Table IV) were obtained on a KRATOS MS-50 double focusing mass spectrometer of 3000 dalton mass range, using 8 kV accelerating voltage. The instrument was operating under computer control. To obtain high quality data, a DS-90 data system in "raw data" acquisition was used: this gives peak shapes and provides better sensitivity than the usual operation mode which converts analogue signals to centroids. For FAB, a saddle field atom gun was used with Xe gas ($2 \times 10^{-5}$ tort pressure indicated on the source ion gauge) at 6 kV voltage and 1 mA current. The samples were dissolved in a 1:1 mixture of MeOH/$H_2O$ containing 0.2N HCl or alternatively in dimethylformamide (DMF). Then, 1 microliter of this solution was mixed with 1 microliter of thioglycerol matrix eventually containing a 1N acetic acid on the target.

The products were purified by reverse-phase column chromatography on silanized Silica-gel (0.063–0.2 mm; Merck). The ratio between crude product and Silica-gel was generally 1:100 by weight. Columns were developed with linear step gradients from 0–10% to 40–70% of $CH_3CN$ in 0.01N acetic acid (or $H_2O$), in 16–24 h at a flow-rate of 200–400 mL/h, while collecting 15–25 mL fractions.

Reactions, column eluates and final products were checked by HPLC analyses (TABLE V) which were performed on a column HIBAR RT 250-4 (Merck) pre-packed with LICHROSORB RP-8 (10 micron), using a VARIAN 5500 LC pump equipped with a 20 microliter loop injector RHEODYNE 7125 and a VARIAN 2050 UV variable detector. Chromatograms were recorded at 254 nm, using the proper starting glycopeptide antibiotic as internal reference for obtaining the relative $t_R$ (rel. $t_R$) value of the respective derivative. Elutions were carried out at the flow-rate of 2 ml/min by mixing eluent a, 0.2% aqueous $HCO_2NH_4$, with eluent b, $CH_3CN$, according to a linear step gradient programmed as follows:

| minutes:    | 0 | 10 | 20 | 30 | 40 | 50 |
|-------------|---|----|----|----|----|----|
| % of b in a: | 5 | 23 | 26 | 35 | 75 | 5  |

The solvent content and inorganic residue in final powders were determined by thermogravimetry (TG) at 140° C., and after heating the samples at 900° C. in $O_2$ atmosphere, respectively.

TABLE II

| Pentapeptide Compound Example No. | Starting dalbaheptide antibiotic | FORMULA | E.W. | M.W. | pKa1 | pKa2 | pKa3 |
|---|---|---|---|---|---|---|---|
| 1 | Teicoplanin $A_2$ (complex) | — | 642 | | 4.7 | 5.9 | 7.3 |
| 2 | Teicoplanin A2-2 | $C_{88}H_{101}N_9Cl_{22}O_{33}$ | 637 | 1883.7 | 4.1 | 5.9 | 7.3 |
| 3 | L 17054 (T-A3-1) | $C_{72}H_{72}N_7Cl_2O_{28}$ | 549 | 1568.3 | 4.7 | n.d. | n.d. |
| 4 | L 17046 (T-A3-2) | $C_{66}H_{62}N_8Cl_2O_{23}$ | 477 | 1406.2 | 4.6 | 5.8 | 7.5 |
| 5 | L 17392 (aglycon) | $C_{48}H_{49}N_7Cl_2O_{18}$ | 425 | 1203.0 | 4.5 | 5.5 | n.d. |
| 6 | Vancomycin | $C_{66}H_{79}N_9O_{24}Cl_2$ | 430 | 1453.3 | n.d. | 8.3 | 9.4 |
| 7 | Vancomycin aglycon | $C_{53}H_{56}N_8O_{17}Cl_2$ | 390 | 1148 | n.d. | n.d. | n.d. |
| 8 | Ristocetin | $C_{94}H_{114}N_8O_{43}$ | 750 | 2044 | n.d. | 6.2 | 7.8 |
| 9 | A 40926 | $C_{83}H_{92}N_8O_{29}Cl_2$ | 470 | 1735.5 | 4.5 | 5.9 | 7.5 |

E.W. = equivalent weight determined by titration
M.W. = molecular weight calculated from the assigned formula
n.d. = not determined

TABLE III

$^1$H NMR

| Pentapeptide compound Example No. | $CH_2OH$ (delta, ppm) |
|---|---|
| 1 | 3.51 |
| 5 | 3.51 |
| 6 | 3.28 |
| 7 | 3.35 |
| 8 | 3.38/3.51* |
| 9 | 3.27 |

*The first value refers to the methylene group deriving from the reductive cleavage while the second value refers to the methylene group deriving from the reduction of the carboxymethyl function.

TABLE IV

FAB MS*

| Pentapeptide compound Example No. | $(M + H)^+$ |
|---|---|
| 1 | n.d |
| 2 | 1882.7 |
| 3 | 1567.4 |
| 4 | 1405.4 |
| 5 | 1202.3 |
| 6 | 1452.5 |
| 7 | n.d |
| 8 | 2043.7 |
| 9 | 1735.5 |

*Mass numbers refer to the lowest mass isotope of a cluster.
n.d.: not determined

TABLE V

HPLC ANALYSIS

| Pentapeptide compound Example No. | $t_r$ (min) | rel. $t_r$ |
|---|---|---|
| 1 | (a) | (a) |
| 2 | 15.3 | 0.96 |
| 3 | 10.2 | 0.98 |
| 4 | 10.9 | 0.93 |
| 5 | 11.6 | 0.92 |
| 6 | 7.6 | 0.79 |
| 7 | 12.8 | 0.72 |
| 8 | 8.5 | 0.87 |
| 9 | 20.2 | 0.91 |

(a) the value is not given as the product is a complex; for the component 2 of said complex reference can be made to compound of example 2

EXAMPLE 1

Preparation of the reductive cleavage product of Teicoplanin $A_2$ complex (pentapeptide of formula (Ib) wherein $R_1$ is N-($C_9$–$C_{12}$) acyl-beta-D-glucosaminyl, R3 and R4 are both chloro, $R_6$ is a group $OR_7$ wherein $R_7$ N-acetyl-beta-D-glucosaminyl, $R_9$ is alpha-D-mannosyl, $R_2$, $R_5$, $R_{12}$ and $R_{13}$ are hydrogen, and Y is a carboxyacid group.

A suspension of 10 mmol of teicoplanin $A_2$ complex in 600 mL of a mixture $H_2O$/ethanol 65/35 is stirred at 10°–15° C. for 90 min, while adding portionwise 100 g of $NaBS_4$ pellets. A clear solution forms which is stirred at room temperature for 5 hours then it is diluted with 1 L of MeOH and 0.5 L of EtOH and slowly poured into a solution of 200 mL of acetic acid in 0.5 L of MEOW. The solvents are evaporated at 35° C. under reduced pressure and the jelly residue is redissolved in 1 L of $H_2O$. The resulting solution is loaded at the top of a column of 200 g of silanized silica-gel in $H_2O$. After eluting with 2 L of $H_2O$, the column is developed with a linear step gradient from 10% to 80% of $CH_3CN$ in 0.01N acetic acid, in 15 hours at the flow rate of 400 ml/h while collecting 25 ml fractions.

The fractions containing pure product are pooled and the solvents are evaporated, at 40° C. under reduced pressure, in the presence of butanol to avoid foaming. The solid residue is collected, washed with 200 mL of diethyl ether and dried at room temperature in vacuo for 3 days to give a yield of 82% of the pentapeptide of the title.

EXAMPLE 2

Preparation of the reductive cleavage product of teicoplanin $A_2$ component 2 (pentapeptide of formula (Ib) wherein $R_1$ is N(8-methylnonanoyl)-beta-D-glucosaminyl, R3 and R4 are both chloro, $R_6$ is a group $OR_7$ wherein $R_7$ is N-acetyl-beta-D-glucosaminyl, $R_9$ is alpha-D-mannosyl, $R_2$, $R_5$, $R_{12}$ and $R_{13}$ are hydrogen, and Y is a carboxyacid group.

By substantially following the same procedure of Example 1 but starting from teicoplanin $A_2$ component 2 instead of teicoplanin $A_2$ complex a yield of 84% of the pentapeptide of the title is obtained.

EXAMPLE 3

A—Preparation of the reductive cleavage product of antibiotic L 17054 (pentapeptide of formula (Ib) wherein $R_1$ is hydrogen, R3 and R4 are both chloro, $R_6$ is a group $OR_7$ wherein $R_7$ is N-acetyl-beta-D-glucosaminyl, $R_9$ is alpha-D-mannosyl, $R_2$, $R_5$, $R_{12}$ and $R_{13}$ are hydrogen, and Y is a carboxyacid group.

A suspension of 16 g of antibiotic L 17054 (T-A3-1, ref. 39) is stirred at 10°–15° C. in a mixture $H_2O$/ethanol 65/35 (600 ml.) for 90 min, while adding portionwise 100 g of $NABH_4$ pellets. By essentially following the procedure described in the first part of Example 1 an aqueous solution is obtained which is then loaded at the top of a column of 200 g of silanized silica-gel in $H_2O$. The column is eluted with 2 L of $H_2O$ and then developed with a linear step gradient from 10% to 80% of $CH_3CN$ in $H_2O$ in 15 hours at the flow rate of 400 mL/h, while collecting 25 mL fractions. Then the fractions containing pure products are treated as in Example 1 to yield 75% of the pentapeptide of the title.

B—Preparation of the reductive cleavage product of antibiotic L 17054 (same pentapeptide of example 3A) starting from compound of Example 1 (or from compound of Example 2).

A solution of 2 g (1 mmol) of the pentapeptide compound of Example 1 (or pentapeptide compound of Example 2) in 200 mL of 90% aqueous trifluoroacetic acid (TFA) is stirred at room temperature for 8 hours, then 300 mL of diethyl ether is added. The solid precipitate is collected and purified by column chromatography as described in Example 3A above to yield 1.25 g (65%) of pentapeptide of the title as the ditrifluoroacetate.

EXAMPLE 4

A.—Preparation of the reductive cleavage product of antibiotic L 17046 (pentapeptide of formula Ib wherein $R_1$, $R_2$, $R_5$, $R_9$, $R_{12}$ and $R_{13}$ are hydrogen, R3 and R4 are both chloro, $R_6$ is a group $OR_7$ wherein $R_7$ is N-acetyl-beta-D-glucosaminyl, and Y is a carboxyacid group.

By substantially following the procedure of Example 3A but using antibiotic L 17046 (T-A3-2, ref. 39) as starting material instead of antibiotic L 17054 (T-A3-2, ref. 39) a 62% yield of the pentapeptide of the title is obtained.

B.—Preparation of the reductive cleavage product of antibiotic L 17046 (T-A3-2, ref. 39) starting from the compound of Example 1 (or compound of Example 2, or compound of Example 3).

Dry HCl is bubbled at room temperature into a stirred suspension of 1 mmol of compound of Example 1 (or compound of Example 2 or compound of Example 3) in 100 mL of dimethoxyethane (DME) for 6 hours; afterwards, the solvent is evaporated at 40° C. under reduced pressure. The solid residue is chromatographed according to the method described in Example 3A above to give the pentapeptide of the title, as the di-hydrochloride, in a 60% yield.

EXAMPLE 5

A—Preparation of the reductive cleavage product of antibiotic 1 17392 (pentapeptide of formula (Ib), wherein $R_1$, $R_2$, $R_5$, $R_9$, $R_{12}$ and $R_{13}$ are hydrogen, R3 and R4 are both chloro, $R_6$ is a group $OR_7$ wherein $R_7$ hydrogen, and Y is a carboxyacid group.

By essentially following the procedure described in Example 3A but using antibiotic L 17392 (deglucoteicoplanin, teicoplanin aglycone, ref. 39) as starting material instead of antibiotic L 17054 the title compound is obtained with a 47% yield.

B—Preparation of the reductive cleavage product of antibiotic L 17392 starting from compound of Example 1 (or compound of Example 2 or compound of Example 3 or compound of Example 4).

Dry HCl is bubbled at 70° C. into a stirred suspension of 1 mmol of one of the above pentapeptides (Examples 1, 2, 3 or 4) in 100 mL of 2,2,2-trifluoroethanol (TFE) for 16 hours. The insoluble product is collected and chromatographed as described in Example 3A above to give the pentapeptide of the title as the di-hydrochloride in a 25% yield.

EXAMPLE 6

Preparation of the reductive cleavage product of vancomycin (pentapeptide of formula (Ic).

A suspension of 10 mmol of vancomycin in 600 mL of a $H_2O$/ethanol 65/35 mixture is stirred at 10°–15° C. for 90 min, while adding portionwise 75.6 g of $NABS_4$ in pellets. A clear solution forms which is stirred at room temperature for 48 hours. After adding 1 L of methanol and 0.5 L of ethanol, the resulting solution is slowly poured into a solution of an excess of acetic acid in 0.5 L of methanol, then the solvents are evaporated at 35° C. under reduced pressure. The jelly residue, dissolved in 1 L of $H_2O$, is purified by reverse-phase column chromatography as described in Example 3A above. Fractions containing pure (HPLC) product are pooled and the solvents are evaporated, at 40° C. under reduced pressure, in the presence of butanol to avoid foaming. The solid residue is collected, washed with 200 mL of diethyl ether and dried at room temperature in vacuo over KOH for three days, to yield the final pentapeptide of the title in a 61% yield.

EXAMPLE 7

Preparation of the reductive cleavage product of vancomycin aglycon (pentapeptide of formula (Ic), wherein the sugar moiety is replaced by hydrogen)

A suspension of 10 mmol of the aglycon of vancomycin (prepared by reaction of vancomycin with trifluoroacetic acid (TFA) according to the procedure described by Nagarajan, R. and Shabel A. A. in J. Chem. Soc. Chem. Comm. 1988, 1306) in 600 mL of a $H_2O$/ethanol 65/35 mixture is stirred at 10°–15° C. for 90 min, while adding portionwise 94.5 g of $NaBH_4$ pellets. The reaction mixture is stirred at room temperature for 36 hours. Then it is added 1 L of methanol and 0.5 L of ethanol and the resulting solution is treated substantially in the same way as in Example 5. The final yield of the pentapeptide of the title is 36%.

EXAMPLE 8

Preparation of the reductive cleavage product of ristocetin (pentapeptide of formula Ia, wherein Y is hydroxymethyl).

A suspension of 10 mmol of ristocetin in 600 mL of a $H_2O$/ethanol 65/35 mixture is stirred at 10°–15° C. for 90 min, while adding portionwise 45.36 g of $NaBH_4$ pellets. A clear solution forms which is stirred at room temperature for 16 hours. The solution is treated according to the procedure described in Example 5 giving the pentapeptide of the title in a 59% yield.

EXAMPLE 9

Preparation of the reductive cleavage product of antibiotic A/40926.

A suspension of 10 mmol of antibiotic A/40926 in 600 ml of a H$_2$O/ethanol 65/35 mixture is stirred at 10°–15° C. for 90 min, adding portionwise 30.24 g of NABS$_4$ in pellets. The solution is stirred at room temperature for 24 hours. Then the clear solution is treated according to the procedure described in Example 5 giving a yield of 68% of the pentaptide compound having the same structure as A/40926 (ref. 23) with the exception that the peptidic bond between the second and third amino acid (starting from the right) is split and the carbonyl function of the second amino acid is reduced to hydroxmethyl.

REFERENCES

1. Sztaricskai, F., and Bognat, R. The Chemistry of the Vancomycin Group of Antibiotics. In: Recent Developments in the Chemistry of Natural Carbon Compounds. Vol.X. R. Bognar and Cs. Szantay (Eds.). Akadémiai Kiado 1984; 91–201.
2. Katrukha, G. S. and Silaev, A. B. The Chemistry of Glycopeptide Antibiotics of the Vancomycin group. In: Chemistry of Peptides and Proteins. Vol.3. W. Voelter, E. Bayer, Y. A. Ovchinnikov and V. T. Ivanov (Eds.). W. de Gruyter and Co. 1986; 289–306.
3. U.S. Pat. No. 4,456,593.
4. Rajananda, V., Norris A. F., and Williams D. H.: Characterization of beta-hydroxytyrosine unit in ristocetin A. J. Chem. Soc. Perkin Trans. I, 1979: 29–31.
5. Bognat, R. Sztaricskai, F., dunk, M. E. and James, J. Structure and stereochemistry of ristosamine. J. Org. Chem. 1974,39: 2971–2974.
6. Williams, D. H., Rajananda, V., Bojesen, G. and Williamson, M. P. Structure of the antibiotic ristocetin A. J. C. S. Chem. Comm. 1979:906–908.
7. Debono, M., Merkel, K. E., Molloy, R. M., Barnhart, M., Presti, E., Hunt, A. H. and Hamill, R. L. Actaplanin, new glycopeptide antibiotics produced by Actinoplanes missouriensis. The isolation and preliminary chemical characterization of actaplanin, J Antibiot 1984; 37:85–95.
8. Hunt, A. H., Elzey, T. K., Merkel, K. E. and Debono, M. Structures of the actaplanins. J Org Chem 1984; 49:641–645.
9. Borghi, A., Coronelli, C., Faniuolo, L., Allievi, G., Pallanza, R. and Gallo, G. G. Teichomycins, new antibiotics from Actinoplanes teichomyceticus nov. sp. IV. Separation and characterization of the components of teichomycin (teicoplanin). J Antibiot 1984; 37:615–626.
10. Coronelli, C., Gallo, G. G. and Cavalleri, B. Teicoplanin: chemical, physico-chemical and biological aspects. Farm Ed Sci 1987; 42:767–
11. Barna, J. C. J., Williams, D. H., Stone, D. J. M., Leung, T.-W.C. and Doddrell, D. M. Structure elucidation of the teicoplanin antibiotics. J Am Chem Soc 1984; 106:4895–4902.
12. Michel, K. H., Shah, R. M. and Hamill, R. L. A35512, a complex of new antibacterial antibiotics produced by Streptomyces candidus. I. Isolation and characterization. J Antibiot 1980; 33:1397–1406.
13. Harris, C. M. and Harris, T. M. Structural studies of glycopeptide antibiotic A35512B. Identification of the diphenyl ether-type bis (amino acid). Tetrahedron 1983; 39:1661–1666.
14. Eggerr, J. H., Michel K. H., Boeck, L. D., Nakatsukasa, W. M. and Kastner, R. E. A41030, a complex of novel glycopeptide antibiotics. Discovery, fermentation, isolation and characterization. 23rd Intersci Conf Antimicrob Agents Cnemother (October 24–26, Las Vegas) 1983; Abst 440.
15. Hunt, A. H. Dorman, D. E., Debono, M. and Molloy, R. M. Structure of Antibiotic A41030A. J Org Chem 1985; 50:2031–2035.
16. Boeck, L. D., Mertz, F. P. A47934, a novel glycopeptide-aglycone antibiotic produced by a strain of Streptomyces toyocaensis. Taxonomy and fermentation studies. J Antibiot 1986; 39:1533–1540.
17. Hunt, A. H., Occolowitz, J. L., Debono, M., Molloy, R. M. and Maciak, G. M. A47934 and A41030 factors-new glycopeptides and glycopeptide aglycones: structure determination. 23rd Intersci Conf Antimicrob Agents Chemother (October 24–26, Las Vegas) 1983; Abst 441.
18. Sittin, R. D., Chan, G. W., Dingerdissen, J. J., Holl, W., Hoover, J. R. E., Valenta, J. R., Webb, L. and Snader, K. M. Aridicins, novel glycopeptide antibiotics. II. Isolation and characterization, J Antibiot 1985; 38:581–571.
19. Jells, P. W., Mueller, L., DeBrosse, C., Heald, S. L. and Fisher, R. Structure of aridicin A. An integrated approach employing 2D NMR, energy minimization, and distance constraints. J Am Chem Soc 1986; 108:3063–3075.
20. Roberts, G. D., Cart, S. A., Rottschaefer, S. and Jells, P. W. Structural characterization of glycopeptide antibiotics related to vancomycin by Fast Atom Bombardment Mass Spectrometry. J Antibiot 1985; 38:713–720.
21. European Patent Appl. Publ. No. 177,882.
22. Riva, E., Zanol, M., Selva, E. and Borghi, A. Column purification and HPLC determination of teicoplanin and A40926. Chromatographia 1987; 24:295–301.
23. Waltho, J. P., Williams, D. H., Selva, E. and Ferrari, P. Structure elucidation of the glycopeptide antibiotic complex A40926. J Chem Soc, Perkin Trans I, 1987; 2103–2107.
24. Folena-Wasserman, G., Poehland, L. B., Yeung, E. W-K., Staiger, D., Killmet, L. B., Snader, K., Dingerdissen, J. J. and Jells, P. W. Kibdelins (AAD-609), novel glycopeptide antibiotics. isolation, purification, and structure. J Antibiot 1986; 39:1395–1406.
25. Christensen, S. B., Allaudeen, H. S., Burke, M. R., Cart, S. A., Chung, S. K., DePhillips, P., Dingerdissen, J. J., DiPaolo, M., Giovenella, A. J., Heald, S. L., Killmet, L. B., Mico, B. A., Mueller, L., Pan, C. B., Poebland, B. L., Rake, J. B., Roberts, G. D., Shearer, M. C., Sitrin, R. D., Nisbet, L. J. and Jeffs, P. W. Parvodicin, a novel glycopeptide from a new species, Actinomadura parvosata: discovery, taxonomy, activity and structure elucidation, J Antibiot 1987; 40:970–990.
26. European Patent Appl. Publ. No. 265,143.
27. European Patent Appl. Publ. No. 132,116.
28. European Patent Appl. Publ. No. 301,785.
29. European Patent Appl. Publ. No. 255,256.
30. U.S. Pat. No. 4,322,343.
31. U.S. Pat. No. 4,563,442.
32. U.S. Pat. No. 4,504,467.
33. U.S. Pat. No. 4,497,802.
34. Huber, F. M., Michel, K. H., Hunt, A. J., Martin, J. W., and Molloy, R. M. Preparation and characterization of some bromine analogs of the glycopeptide antibiotic actaplanin. J. Antibiot. 1988; 41:798–801.
35. U.S. Pat. No. 2,951,766.
36. Cometti, A., Gallo, G. G., Ketternring, J., Pallanza, R., Panzone, G. B., Tuan, G., and Zerilli, L. F. Isolation and structure determination of the main related substances of teicoplanin, a glycopeptide antibiotic. Il Farmaco, Ed. Sci., 1988; 43:1005–1018.

37. Borghi, A., Antonini, P., Zanol, M., Ferrari, P., Zerilli, L. F., and Lancini. G. C. Isolation and structure determination of two new analogs of teicoplanin, a glycopeptide antibiotic. J. Antibiotic 1989; 42:361–366.

38. Malabarba, A., Ferrari, P., Gallo, G. G., Kettenring, J. and Cavalle ri B. Teicoplanin, antibiotics from *Actinoplanes teichomyceticus* nov. sp. VII. Preparation and NMR characteristic of the aglycone of teicoplanin. J Antibiot 1986; 39:1430–1442.

39. Malabarba, A., Strazzolini, P., DePaoli, A., Landi, M., Berti, M. and Cavalleri, B. Teicoplanin, antibiotics from *Actinoplanes teichomyceticus* nov. sp. VI. Chemical degradation: physico-chemical and biological properties of acid hydrolysis products. J Antibiot 1984; 37:988–999.

40. European Patent Appl. Publ. No. 301 247.
41. European Patent Appl. Publ. No. 216 775.
42. European Patent Appl. Publ. No. 326 873.
43. European Patent Appl. Publ. No. 290 922.
44. European Patent Appl. Publ. No. 376 041.
45. European Patent Appl. Publ. No. 316 712.
46. European Patent Appl. Set. No. 90104234.1 (corresponding to U.S. pat. appln. Ser. No.499,221).
47. European Patent Appl. Publ. No. 228 015.
48. European Patent Appl. Publ. No. 240 609.
49. International Patent Appl. Publ. No. WO/88/02755.
50. European Patent Appl. Publ. No. 254 999.

51. Kamogashira, T., Nishida, T. and Sugawara, M. A new glycopeptide antibiotic, OA-7653, produced by *Streptomyces hygroscopicus* subsp. hiwasaensis. Agric Biol Chem 1983; 47:499–506.

52. Jeffs, P. W., Yellin, B., Mueller, L. and Heald, S. L. Structure of the antibiotic OA-7653. J Org Chem 1988; 53:471–477.

53. Boeck, L. D., Mertz, F. P., Wolter, R. K. and Biggens, C. E. N-Demethyl vancomycin, a novel antibiotic produced by a strain of *Nocardia orientalis*. Taxonomy and fermentation. J Antibiot 1984; 37:446–453.

54. Hunt, A. H., Marconi, G. G., Elzey, T. K. and Boehn, M. M. A51568A: N-Demethylvancomycin. J Antibiot 1984; 37:917–919.

55. European Patent Appl. Publ. No. 159,180.
56. European Patent Appl. Publ. No. 231 111.

57. Tsuji, N., Kobayashi, M., Kamigauchi, T., Yoshimura, Y. and Terui, Y. New glycopeptide antibiotics. I. The structures of orienticins. J Antibiot 1988; 41:819–822.

58. Gauze, G. F., Brazhnikova, M. G., Laiko, A. V., Sveshnikova, M. A., Preobrazhenskaya, T. P., Fedorova, G. B., Borisova, V. N., Tolstykh, I. V., Yurina, M. S., Pokras, L. S., Goldberg, L. E., Malkova, I. V. and Stepanova, E. S. Eremomycin, a novel cyclic glycopeptide antibiotic. Antibiot Med Biotecknol 1987; 32:571–576.

59. Brazhnikova, M. G. Properties of eremomycin, a new glycopeptide antibiotic. 2nd Int Symp on "New Bioactive Metabolites from Microorganisms" (May 2–7, Gera) 1988; Pose 40.

60. Berdnikova, T. F., Tokareva, N. L., Abramova, E. A., Dokshina, N. Y., Potapova, N. P. and Lomakina, N. N. Structure of the aglycone of eremomycin, a novel antibiotic of the group of polycyclic glycopeptides. Antibiot Kimioter 1988; 33:566–70.

61. Lomakina, N. N., Tokareva, N. L. and Potapova, N. P. Structure of eremosamine, an amino sugar from eremomycin. Antibiot Kimioter 1988; 33:726–729.

62. Riva, E., Gastaldo, L., Beretta, M. G., Ferrari, P., Zerilli, L. F., Cassani, G., Goldstein, B. P., Berti, M., Parenti, F. and Denaro, M. A42867, a novel glycopeptide antibiotic. J Antibiot. 1989; 42:497–505.

63. Hamill, R. L., Baker, P. J., Berry, D. M., Debono, M., Molloy, R. M. and Moreland, D. S. A82846, a new glycopeptide complex, produced by *Amycolatopsis orientalis*. 2.Isolation and characterization. 28th Intersci Conf Antimicrob Agents Chemother (October 23–26, Los Angeles) 1988; Abst 975.

64. Hunt, A. H., Occolowitz, J. L., Debono, M., Molloy, R. M. A82846, a new glycopeptide complex, produced by *Amycolatopsis orientalis*. 3. Structure determination. 28th Intersci Conf Antimicrob Agents Chemother (October 23–26, Los Angeles) 1988; Abst 976.

65. Tsuji, No, Kamigauchi, T., Kobayashi, M. and Terui, Y. New glyco peptide antibiotics: II. The isolation and structures of chloro orienticins. J Antibiot 1988; 41:1506–1510.

66. European Patent Appl. Publ. No. 273 727.
67. European Patent Appl. Publ. No. 159 863.
68. European Patent Appl. Publ. No. 201 251.
69. U.S. Pat. No. 4,698,327.
70. U.S. Pat. No. 4,639,433.
71. U.S. Pat. No. 4,643,987.

72. Harris C. M., Kannan R., Kopecka H., and Harris T. M. The role of the chlorine substituents in the antibiotic vancomycin:preparation and characterization of mono- and didechlorovancomycin. J. Am. Chem. Soc. 1985; 107:6652–6658.

73. McCormick, M. H., Stark, W. M., Pittenger, G. E., Pittenger, R. C. and McGuire, J. M. Vancomycin, a new antibiotic. I.Chemical and biological properties. In: Antibiotics Annual 1955–1956. H. Welch and F. Marti-Ibanez (Eds.). Medical Encyclopedia, Inc. 1956; 606–611.

74. Harris, C. M., Kopecka, H. and Harris, T. M. Vancomycin: structure and transformation to CDP-I. J Am Chem Soc 1983; 105:6915–6922.

75. Batta, G., Sztaricskai, F., Csanadi, J., Kamaromi, I. and Bognat, R. $^{13}C$ NMR study of actinoidins: carbohydrate moieties and their glycosidic linkages. J Antibiot 1986; 39:910–913.

76. Heald, S. L., Mueller, L. and Jeffs, P. W. Actinoidins A and A2: structure determination using 2D NMR methods. J Antibiot 1987; 40:630–645.

77. Okazaki, T., Enokita, R., Miyaoka, H., Takatsu, T. and Torkiata, A. Chloropolysporins A, B and C, novel glycopeptide antibiotics from Faenia interjecta sp.nov. I. Taxonomy of producing organism. J Antibiot 1987; 40:917–923.

78. Takatsu, T., Nakajima, M., Oyajima, S., Itoh, Y., Sakaida, Y., Takahashi, S. and Haneishi, T. Chloropolysporins A, B and C, novel glycopeptide antibiotics from *Faenia interjecta* sp. nov. II. Fermentation, isolation and physico-chemical characterization. J Antibiot 1987; 40:924–932.

79. Takatsu, T., Takahashi, S., Nakajima, M., Haneishi, T., Nakamura, T., Kuwano, H. and Kinoshita, T. Chloropolysporins A, B and C, novel glycopeptide antibiotics from *Faenia interjecta* sp. nov. III. Structure elucidation of chloropolysporins. J Antibiot 1987; 40:933–940.

80. Dingerdissen, J. J., Sitrin, R. D., DePhillips, P. A., Giovenella, A. J., Grappel, S. F., Mehta, R. J., Oh, Y. K., Pan, C. H., Roberts, G. D., Shearer, M. C. and Nisbet, L. J. Actinoidin A2 a novel glyco peptide: production, preparative HPLC separation and characterization. J Antibiot 1987; 40:165–172.

81. Japanese Pat. Appln. Publ. No. 63017897 (Farmdoc Abstract 88-061310).

82. Herrin, T. R., Thomas, A. M., Perun, J. T., Mao, J. C., and Fesik. S. W. Preparation of biologically active ristocetin derivatives: replacements of the 1'-amino group. J. Med. Chem. 1985; 28:1371–1375.

83. Kunstmann, M. P., Mitscher, L. A., Porter, J. N., Shay, A. J. and Darken, M. A. LL-AV290, a new antibiotic.

I. Fermentation, isolation, and characterization. Antimicrob Agents Chemother 1968; 242–245.

84. McGahren, W. J., Leese, R. A., Barbatscni, F., Morton, G. O., Kuck, N. A. and Ellestad, G. A. Components and degradation compounds of the avoparcin complex. J Antibiot 1983; 36:1671–1682.

85. McGahren, W. J., Martin, J. H., Morton, G. O., Bargreaves, R. T., Leese, R. A., Lovell, F. M., Ellestad, G. A., O'Brien, E. and Holker, J. S. E. Structure of avoparcin components. J Am Chem Soc 1980; 102:1671–1684.

86. European Patent Appl. Publ. No. 255 299.

87. Arjuna Rao, V., Ravishankar, D., Sadhukhan, A. K., Ahmed, S. M., Goel, A. K., Prabhu, N. S., Verma, A. K., Venkateswarlu, A., Allaudeen, H. S., Hedde, R. H. and Nisbet, L. J. Synmonicins: a novel antibiotic complex produced by *Synnemomyces mamnoorii* gen. et. sp. nov. I. Taxonomy of the producing organism, fermentation and biological properties, 26th Intersci Conf Antimicrob Agents Chemother (September 28–October 1, New Orleans) 1986; Abst 939.

88. Verma, A. K., Prakash, R., Carr, S. A., Roberts, G. D. and Sittin, R. D. Synmonicins: a novel antibiotic complex. II. Isolation and preliminary characterization. 26rd Intersci Conf Antimicrob Agents Chemother (September 28–October 1, Las Vegas) 1986; Abst 940.

89. Pant, N. and Hamilton, A.D. Carboxylic acid complexation by a synthetic analogue of the "carboxylate-binding pocket" of vancomycin. J Am Chem Soc 1988; 110:2002–2003.

90. Ramakrishnan, N., and Schabel, A. A. Selective cleavage of vancosamine, glucose and N-methylleucine from vancomycin and related antibiotics. J. Chem. Soc. Comm.: 1988; 1306–1307.

91. Nieto, M. and Perkins, H. R. The specificity of combination between ristocetin and peptides related to bacterial cell wall mucopeptide precursors. Biochm. J. 1971; 124:845–852.

92. European Pat. Appln. Publ. No. 339 982.

93. European Pat. Appln. Publ. No. 365 319.

94. International Pat. Appln. Publ. WO 89/07612.

95. European Pat. Appln. Publ. No. 356 894.

96. international Pat. Appln. No. WO 89/02441.

97. European Pat. Appln. Ser. No. 90105891.7 of Mar. 28, 1990.

We claim:

1. A process for preparing a pentapeptide antibiotic of formula (I)

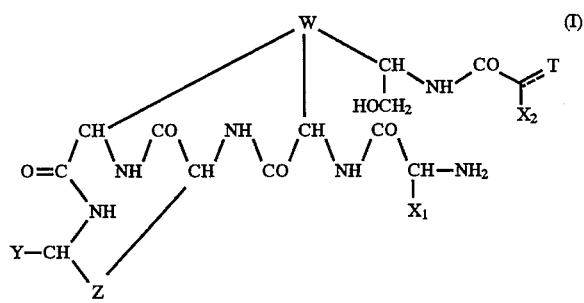

wherein W, Z, $X_1$, $X_2$ and T represents the structural groups present in pentapeptide antibiotics of a dalbaheptide, where Y represents a carboxy acid group, a lower alkyl carboxy ester, or a hydroxymethyl group; the salts of the pentapeptide with acids or bases; or the inner salts of the pentapeptide, which comprises submitting a dalbapeptide antibiotic of formula (II)

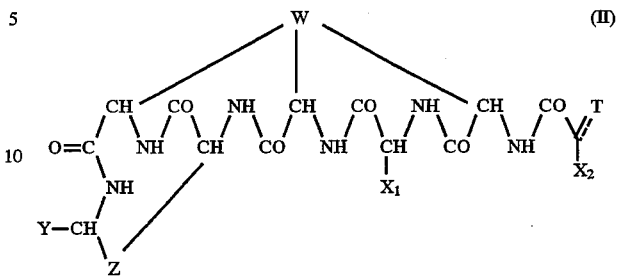

wherein W, Z, $X_1$, $X_2$, and T have the same meanings as above and Y represents a carboxy acid group, a lower alkyl carboxy ester, or hydroxy methyl group, to a reductive cleavage with an alkali metal borohydride, preferably selected from sodium borohydride, potassium borohydride and sodium cyanoborohydride, at a temperature between 0° C. and 40° C.

2. The process as in claim 1 wherein the reductive cleavage is carried out in a hydroalcoholic medium wherein the alcohol is a lower ($C_1$–$C_4$) linear or branched alkanol and the ratio of water to alkanol ranges between 40/60 and 90/10(v/v).

3. The process according to claim 2 wherein the dalbaheptide of formula (II) is Teicoplanin A2 complex.

4. The process according to claim 2 wherein the dalbaheptide of formula (II) is Teicoplanin A2 component 2.

5. The process according to claim 2 wherein the dalbaheptide of formula (II) is L17054.

6. The process according to claim 2 wherein the dalbaheptide of formula (II) is L17046.

7. The process according to claim 2 wherein the dalbaheptide of formula (II) is L17392.

8. The process according to claim 2 wherein the dalbaheptide of formula (II) is Vancomycin.

9. The process according to claim 2 wherein the dalbaheptide of formula (II) is Vancomycin aglycone.

10. The process according to claim 2 wherein the dalbaheptide of formula (II) is a reductive cleavage product of Ristocetin wherein Y is represented by hydroxymethyl.

11. The process according to claim 2 wherein the dalbaheptide of formula (II) is a reductive cleavage product of antibiotic A40926.

12. The process as in claim 1 for producing a pentapeptide compound wherein the sugar moieties characterizing its dalbaheptide precursor are totally or partially hydrolyzed which include the additional step of submitting the pentapeptide antibiotic resulting from the reductive cleavage process to selective acid hydrolysis.

13. A process as in any of claims 2 to 12 wherein the reductive cleavage reaction is carried out at a pH between 8 and 10 and the molar ratio between the alkali metal borohydride and the dalbaheptide antibiotic starting material is between 50 and 300.

14. The process as in any off claims 1 wherein the reductive cleavage reaction is carried out for a period of time between 10 and 48 hours.

* * * * *